United States Patent
Lev et al.

(10) Patent No.: US 9,283,324 B2
(45) Date of Patent: Mar. 15, 2016

(54) FLUID TRANSFER DEVICES HAVING CARTRIDGE PORT WITH CARTRIDGE EJECTION ARRANGEMENT

(71) Applicant: MEDIMOP Medical Projects Ltd., Ra'anana (IL)

(72) Inventors: Nimrod Lev, Savion (IL); Niv Ben Shalom, Netanya (IL)

(73) Assignee: Medimop Medical Projects, Ltd, Ra'anana (IL)

( * ) Notice: Subject to any disclaimer, the term of this patent is extended or adjusted under 35 U.S.C. 154(b) by 0 days.

(21) Appl. No.: 14/385,212

(22) PCT Filed: Apr. 7, 2013

(86) PCT No.: PCT/IL2013/050313
§ 371 (c)(1),
(2) Date: Sep. 15, 2014

(87) PCT Pub. No.: WO2013/150538
PCT Pub. Date: Oct. 10, 2013

(65) Prior Publication Data
US 2015/0088078 A1    Mar. 26, 2015

(30) Foreign Application Priority Data

Apr. 5, 2012 (IL) .......................... 219065

(51) Int. Cl.
*A61M 5/178* (2006.01)
*A61J 1/14* (2006.01)
(Continued)

(52) U.S. Cl.
CPC ............ *A61M 5/1782* (2013.01); *A61J 1/1406* (2013.01); *A61J 1/2089* (2013.01);
(Continued)

(58) Field of Classification Search
CPC ... A61M 5/1782; A61J 1/2096; A61J 1/1406; A61J 1/2089; A61J 1/201; A61J 1/2013; A61J 1/2055; A61J 1/2062; B65B 3/003
See application file for complete search history.

(56) References Cited

U.S. PATENT DOCUMENTS

| 62,333 | A | 2/1867 | Holl |
| 1,021,681 | A | 3/1912 | Jennings |

(Continued)

FOREIGN PATENT DOCUMENTS

| CN | 1950049 A | 4/2007 |
| DE | 1913926 A1 | 9/1970 |

(Continued)

OTHER PUBLICATIONS

Int'l Preliminary Report on Patentability issued May 12, 2014 in Int'l Application No. PCT/IL2013/050316.
(Continued)

*Primary Examiner* — Bhisma Mehta
*Assistant Examiner* — Jenna Zhang
(74) *Attorney, Agent, or Firm* — Panitch Schwarze Belisario & Nadel LLP

(57) ABSTRACT

Fluid transfer devices for use in manual cartridge filling procedures for filling cartridges with liquid drug dosages from medicament containing vials. The fluid transfer devices include a double ended main body having a longitudinal axis, a vial port for telescopic receiving a drug vial and a cartridge port for slidingly receiving a leading cartridge end. The cartridge port includes a cartridge securing arrangement for releasably securing a leading cartridge end therein and a cartridge ejection arrangement for at least partially ejecting a cartridge therefrom for assisting manual sliding ejection of a filled cartridge. The cartridge port can include either a combined cartridge securing and ejection arrangement or a discrete cartridge securing arrangement and a discrete cartridge ejection arrangement.

7 Claims, 13 Drawing Sheets

(51) Int. Cl.
*A61J 1/20* (2006.01)
*A61J 1/06* (2006.01)

(52) U.S. Cl.
CPC .............. *A61J 1/2096* (2013.01); *A61J 1/062* (2013.01); *A61J 1/201* (2015.05); *A61J 1/2013* (2015.05); *A61J 1/2055* (2015.05); *A61J 2001/2013* (2013.01); *A61J 2001/2055* (2013.01)

(56) References Cited

U.S. PATENT DOCUMENTS

| | | | |
|---|---|---|---|
| 1,704,817 A | 3/1929 | Ayers | |
| 1,930,944 A | 10/1933 | Schmitz, Jr. | |
| 2,326,490 A | 8/1943 | Perelson | |
| 2,931,668 A | 4/1960 | Baley | |
| 2,968,497 A | 1/1961 | Treleman | |
| 3,059,643 A | 10/1962 | Barton | |
| D198,499 S | 6/1964 | Harautuneian | |
| 3,225,763 A | 12/1965 | Waterman | |
| 3,484,849 A | 12/1969 | Huebner et al. | |
| 3,618,637 A | 11/1971 | Santomieri | |
| 3,757,981 A | 9/1973 | Harris, Sr. et al. | |
| 3,788,524 A | 1/1974 | Davis et al. | |
| 3,822,700 A | 7/1974 | Pennington | |
| 3,826,261 A | 7/1974 | Killinger | |
| 3,872,992 A | 3/1975 | Larson | |
| 3,885,607 A | 5/1975 | Peltier | |
| 3,938,520 A | 2/1976 | Scislowicz et al. | |
| 3,957,052 A | 5/1976 | Topham | |
| 3,977,555 A | 8/1976 | Larson | |
| 3,993,063 A | 11/1976 | Larrabee | |
| 4,020,839 A | 5/1977 | Klapp | |
| 4,051,852 A | 10/1977 | Villari | |
| D248,568 S | 7/1978 | Ismach | |
| 4,109,670 A | 8/1978 | Slagel | |
| 4,121,585 A | 10/1978 | Becker, Jr. | |
| 4,161,178 A | 7/1979 | Genese | |
| 4,187,848 A | 2/1980 | Taylor | |
| 4,203,067 A | 5/1980 | Fitzky et al. | |
| 4,203,443 A | 5/1980 | Genese | |
| 4,210,173 A | 7/1980 | Choksi et al. | |
| D257,286 S | 10/1980 | Folkman | |
| 4,253,501 A | 3/1981 | Ogle | |
| 4,296,786 A | 10/1981 | Brignola | |
| 4,303,067 A | 12/1981 | Connolly et al. | |
| 4,312,349 A | 1/1982 | Cohen | |
| 4,314,586 A | 2/1982 | Folkman | |
| 4,328,802 A | 5/1982 | Curley et al. | |
| 4,335,717 A | 6/1982 | Bujan et al. | |
| D267,199 S | 12/1982 | Koenig | |
| 4,376,634 A | 3/1983 | Prior et al. | |
| D268,871 S | 5/1983 | Benham et al. | |
| 4,392,850 A | 7/1983 | Elias et al. | |
| D270,282 S | 8/1983 | Gross | |
| 4,410,321 A | 10/1983 | Pearson et al. | |
| 4,411,662 A | 10/1983 | Pearson | |
| D271,421 S | 11/1983 | Fetterman | |
| 4,434,823 A | 3/1984 | Hudspith | |
| 4,465,471 A | 8/1984 | Harris et al. | |
| 4,475,915 A | 10/1984 | Sloane | |
| 4,493,348 A | 1/1985 | Lemmons | |
| 4,505,709 A | 3/1985 | Froning et al. | |
| 4,507,113 A | 3/1985 | Dunlap | |
| D280,018 S | 8/1985 | Scott | |
| 4,532,969 A | 8/1985 | Kwaan | |
| 4,564,054 A | 1/1986 | Gustavsson | |
| 4,573,993 A | 3/1986 | Hoag et al. | |
| 4,576,211 A | 3/1986 | Valentini et al. | |
| 4,581,014 A | 4/1986 | Millerd et al. | |
| 4,588,396 A | 5/1986 | Stroebel et al. | |
| 4,588,403 A | 5/1986 | Weiss et al. | |
| D284,603 S | 7/1986 | Loignon | |
| 4,604,093 A | 8/1986 | Brown et al. | |
| 4,607,671 A | 8/1986 | Aalto et al. | |
| 4,614,437 A | 9/1986 | Buehler | |
| 4,638,975 A | 1/1987 | Iuchi et al. | |
| 4,639,019 A | 1/1987 | Mittleman | |
| 4,667,927 A | 5/1987 | Oscarsson | |
| 4,676,530 A | 6/1987 | Nordgren et al. | |
| 4,683,975 A | 8/1987 | Booth et al. | |
| 4,697,622 A | 10/1987 | Swift et al. | |
| 4,721,133 A | 1/1988 | Sundblom | |
| 4,729,401 A | 3/1988 | Raines | |
| 4,735,608 A | 4/1988 | Sardam | |
| 4,743,229 A | 5/1988 | Chu | |
| 4,743,243 A | 5/1988 | Vaillancourt | |
| 4,752,292 A | 6/1988 | Lopez et al. | |
| 4,758,235 A | 7/1988 | Tu | |
| 4,759,756 A | 7/1988 | Forman et al. | |
| 4,778,447 A | 10/1988 | Velde et al. | |
| 4,787,898 A | 11/1988 | Raines | |
| 4,797,898 A | 1/1989 | Martinez | |
| 4,804,366 A | 2/1989 | Zdeb et al. | |
| 4,832,690 A | 5/1989 | Kuu | |
| 4,834,152 A | 5/1989 | Howson et al. | |
| D303,013 S | 8/1989 | Konopka | |
| 4,857,062 A | 8/1989 | Russell | |
| 4,865,592 A | 9/1989 | Rycroft | |
| 4,871,463 A | 10/1989 | Taylor et al. | |
| 4,898,209 A | 2/1990 | Zbed | |
| 4,909,290 A | 3/1990 | Coccia | |
| 4,931,040 A | 6/1990 | Haber et al. | |
| 4,932,944 A | 6/1990 | Jagger et al. | |
| 4,967,797 A | 11/1990 | Manska | |
| D314,050 S | 1/1991 | Sone | |
| D314,622 S | 2/1991 | Andersson et al. | |
| 4,997,430 A | 3/1991 | Van der Heiden et al. | |
| 5,006,114 A | 4/1991 | Rogers et al. | |
| 5,035,686 A | 7/1991 | Crittenden et al. | |
| 5,041,105 A | 8/1991 | D'Alo et al. | |
| 5,045,066 A | 9/1991 | Scheuble et al. | |
| 5,049,129 A | 9/1991 | Zdeb et al. | |
| 5,053,015 A | 10/1991 | Gross | |
| 5,061,248 A | 10/1991 | Sacco | |
| 5,088,996 A | 2/1992 | Kopfer et al. | |
| 5,096,575 A | 3/1992 | Cosack | |
| 5,104,387 A | 4/1992 | Pokorney et al. | |
| 5,113,904 A | 5/1992 | Aslanian | |
| 5,122,124 A | 6/1992 | Novacek et al. | |
| 5,125,908 A | 6/1992 | Cohen | |
| 5,125,915 A | 6/1992 | Berry et al. | |
| D328,788 S | 8/1992 | Sagae et al. | |
| 5,171,230 A | 12/1992 | Eland et al. | |
| 5,201,705 A | 4/1993 | Berglund et al. | |
| 5,201,717 A | 4/1993 | Wyatt et al. | |
| 5,203,771 A | 4/1993 | Melker et al. | |
| 5,203,775 A | 4/1993 | Frank et al. | |
| 5,211,638 A | 5/1993 | Dudar et al. | |
| 5,232,029 A | 8/1993 | Knox et al. | |
| 5,232,109 A | 8/1993 | Tirrell et al. | |
| 5,242,432 A | 9/1993 | DeFrank | |
| 5,247,972 A | 9/1993 | Tetreault | |
| D341,420 S | 11/1993 | Conn | |
| 5,269,768 A | 12/1993 | Cheung | |
| 5,270,219 A | 12/1993 | DeCastro et al. | |
| 5,279,576 A | 1/1994 | Loo et al. | |
| 5,288,290 A | 2/1994 | Brody | |
| 5,300,034 A | 4/1994 | Behnke et al. | |
| 5,301,685 A | 4/1994 | Guirguis | |
| 5,304,163 A | 4/1994 | Bonnici et al. | |
| 5,304,165 A * | 4/1994 | Haber | A61J 1/2089 604/411 |
| 5,308,483 A | 5/1994 | Sklar et al. | |
| 5,312,377 A | 5/1994 | Dalton | |
| 5,328,474 A | 7/1994 | Raines | |
| D349,648 S | 8/1994 | Tirrell et al. | |
| 5,334,163 A | 8/1994 | Sinnett | |
| 5,334,179 A | 8/1994 | Poli et al. | |
| 5,342,346 A | 8/1994 | Honda et al. | |
| 5,344,417 A | 9/1994 | Wadsworth, Jr. | |
| 5,348,548 A | 9/1994 | Meyer et al. | |
| 5,350,372 A | 9/1994 | Ikeda et al. | |
| 5,364,386 A | 11/1994 | Fukuoka et al. | |

(56) References Cited

U.S. PATENT DOCUMENTS

| | | |
|---|---|---|
| 5,364,387 A | 11/1994 | Sweeney |
| 5,374,264 A | 12/1994 | Wadsworth, Jr. |
| 5,385,547 A | 1/1995 | Wong et al. |
| 5,397,303 A | 3/1995 | Sancoff et al. |
| D357,733 S | 4/1995 | Matkovich |
| 5,429,614 A | 7/1995 | Fowles et al. |
| 5,433,330 A | 7/1995 | Yatsko et al. |
| 5,445,630 A | 8/1995 | Richmond |
| 5,445,631 A | 8/1995 | Uchida |
| 5,451,374 A | 9/1995 | Molina |
| 5,454,805 A | 10/1995 | Brony |
| 5,464,111 A | 11/1995 | Vacek et al. |
| 5,464,123 A | 11/1995 | Scarrow |
| 5,466,219 A | 11/1995 | Lynn et al. |
| 5,466,220 A | 11/1995 | Brenneman |
| 5,470,327 A | 11/1995 | Helgren et al. |
| 5,471,994 A | 12/1995 | Guirguis |
| 5,472,022 A | 12/1995 | Michel et al. |
| 5,478,337 A | 12/1995 | Okamoto et al. |
| 5,492,147 A | 2/1996 | Challender et al. |
| D369,406 S | 4/1996 | Niedospial et al. |
| 5,505,714 A | 4/1996 | Dassa et al. |
| 5,509,433 A | 4/1996 | Paradis |
| 5,520,659 A | 5/1996 | Hedges |
| 5,526,853 A | 6/1996 | McPhee et al. |
| 5,527,306 A | 6/1996 | Haining |
| 5,531,695 A | 7/1996 | Swisher |
| 5,547,471 A | 8/1996 | Thompson et al. |
| 5,549,577 A | 8/1996 | Siegel et al. |
| 5,554,128 A | 9/1996 | Hedges |
| 5,566,729 A | 10/1996 | Grabenkort et al. |
| 5,569,191 A | 10/1996 | Meyer |
| 5,573,281 A | 11/1996 | Keller |
| 5,578,015 A | 11/1996 | Robb |
| 5,583,052 A | 12/1996 | Portnoff et al. |
| 5,584,819 A | 12/1996 | Kopfer |
| 5,591,143 A | 1/1997 | Trombley, III et al. |
| 5,603,706 A | 2/1997 | Wyatt et al. |
| 5,607,439 A | 3/1997 | Yoon |
| 5,611,576 A | 3/1997 | Guala |
| 5,616,203 A | 4/1997 | Stevens |
| 5,636,660 A | 6/1997 | Pfleiderer et al. |
| 5,637,101 A | 6/1997 | Shillington |
| 5,641,010 A | 6/1997 | Maier |
| 5,645,538 A | 7/1997 | Richmond |
| 5,647,845 A | 7/1997 | Haber et al. |
| 5,651,776 A | 7/1997 | Appling et al. |
| 5,653,686 A | 8/1997 | Coulter et al. |
| 5,674,195 A | 10/1997 | Truthan |
| 5,676,346 A | 10/1997 | Leinsing |
| 5,685,845 A | 11/1997 | Grimard |
| D388,172 S | 12/1997 | Cipes |
| 5,699,821 A | 12/1997 | Paradis |
| 5,702,019 A | 12/1997 | Grimard |
| 5,718,346 A | 2/1998 | Weiler |
| D393,722 S | 4/1998 | Fangrow, Jr. et al. |
| 5,738,144 A | 4/1998 | Rogers |
| 5,743,312 A | 4/1998 | Pfeifer et al. |
| 5,746,733 A | 5/1998 | Capaccio et al. |
| 5,755,696 A | 5/1998 | Caizza |
| 5,766,211 A | 6/1998 | Wood et al. |
| 5,772,630 A | 6/1998 | Ljungquist |
| 5,772,652 A | 6/1998 | Zielinski |
| RE35,841 E | 7/1998 | Frank et al. |
| 5,776,116 A | 7/1998 | Lopez et al. |
| 5,782,872 A | 7/1998 | Muller |
| 5,806,831 A | 9/1998 | Paradis |
| 5,810,792 A | 9/1998 | Fangrow, Jr. et al. |
| D399,559 S | 10/1998 | Molina |
| 5,817,082 A | 10/1998 | Niedospial, Jr. et al. |
| 5,820,621 A | 10/1998 | Yale et al. |
| 5,827,262 A | 10/1998 | Neftel et al. |
| 5,832,971 A | 11/1998 | Yale et al. |
| 5,833,213 A | 11/1998 | Ryan |
| 5,834,744 A | 11/1998 | Risman |
| 5,839,715 A | 11/1998 | Leinsing |
| 5,853,406 A | 12/1998 | Masuda et al. |
| D405,522 S | 2/1999 | Hoenig et al. |
| 5,871,110 A | 2/1999 | Grimard et al. |
| 5,873,872 A | 2/1999 | Thibault et al. |
| 5,879,337 A | 3/1999 | Kuracina et al. |
| 5,879,345 A | 3/1999 | Aneas |
| 5,887,633 A | 3/1999 | Yale et al. |
| 5,890,610 A | 4/1999 | Jansen et al. |
| 5,891,129 A | 4/1999 | Daubert et al. |
| 5,893,397 A | 4/1999 | Peterson et al. |
| 5,897,526 A | 4/1999 | Vaillancourt |
| 5,899,468 A | 5/1999 | Apps et al. |
| 5,902,280 A | 5/1999 | Powles et al. |
| 5,902,298 A | 5/1999 | Niedospial, Jr. et al. |
| D410,740 S | 6/1999 | Molina |
| 5,911,710 A | 6/1999 | Barry et al. |
| 5,919,182 A | 7/1999 | Avallone |
| 5,921,419 A | 7/1999 | Niedospial, Jr. et al. |
| 5,924,584 A | 7/1999 | Hellstrom et al. |
| 5,925,029 A | 7/1999 | Jansen et al. |
| 5,935,112 A | 8/1999 | Stevens et al. |
| 5,941,848 A | 8/1999 | Nishimoto et al. |
| 5,944,700 A | 8/1999 | Nguyen et al. |
| 5,954,104 A | 9/1999 | Daubert et al. |
| 5,971,181 A | 10/1999 | Niedospial, Jr. et al. |
| 5,971,965 A | 10/1999 | Mayer |
| 5,989,237 A | 11/1999 | Fowles et al. |
| 6,003,566 A | 12/1999 | Thibault et al. |
| 6,004,278 A | 12/1999 | Botich et al. |
| 6,019,750 A | 2/2000 | Fowles et al. |
| 6,022,339 A | 2/2000 | Fowles et al. |
| 6,036,171 A | 3/2000 | Weinheimer et al. |
| 6,039,093 A | 3/2000 | Mrotzek et al. |
| 6,039,302 A | 3/2000 | Cote, Sr. et al. |
| D422,357 S | 4/2000 | Niedospial, Jr. et al. |
| 6,063,068 A | 5/2000 | Fowles et al. |
| D427,308 S | 6/2000 | Zinger |
| D427,309 S | 6/2000 | Molina |
| 6,070,623 A | 6/2000 | Aneas |
| 6,071,270 A | 6/2000 | Fowles et al. |
| 6,080,132 A | 6/2000 | Cole et al. |
| D428,141 S | 7/2000 | Brotspies et al. |
| 6,086,762 A | 7/2000 | Guala |
| 6,089,541 A | 7/2000 | Weinheimer et al. |
| 6,090,091 A | 7/2000 | Fowles et al. |
| 6,090,093 A | 7/2000 | Thibault et al. |
| 6,092,692 A | 7/2000 | Riskin |
| D430,291 S | 8/2000 | Jansen et al. |
| 6,099,511 A | 8/2000 | Devos et al. |
| 6,113,068 A | 9/2000 | Ryan |
| 6,113,583 A | 9/2000 | Fowles et al. |
| 6,117,114 A | 9/2000 | Paradis |
| 6,139,534 A | 10/2000 | Niedospial, Jr. et al. |
| 6,142,446 A | 11/2000 | Leinsing |
| 6,146,362 A | 11/2000 | Turnbull et al. |
| 6,149,623 A | 11/2000 | Reynolds |
| 6,156,025 A | 12/2000 | Niedospial, Jr. et al. |
| 6,159,192 A | 12/2000 | Fowles et al. |
| 6,168,037 B1 | 1/2001 | Grimard |
| 6,171,287 B1 | 1/2001 | Lynn et al. |
| 6,171,293 B1 | 1/2001 | Rowley et al. |
| 6,173,852 B1 | 1/2001 | Browne |
| 6,173,868 B1 | 1/2001 | DeJonge |
| 6,174,304 B1 | 1/2001 | Weston |
| 6,179,822 B1 | 1/2001 | Niedospial, Jr. |
| 6,179,823 B1 | 1/2001 | Niedospial, Jr. |
| 6,206,861 B1 | 3/2001 | Mayer |
| 6,221,041 B1 | 4/2001 | Russo |
| 6,221,054 B1 | 4/2001 | Martin et al. |
| 6,221,065 B1 | 4/2001 | Davis |
| 6,238,372 B1 | 5/2001 | Zinger et al. |
| 6,245,044 B1 | 6/2001 | Daw et al. |
| D445,501 S | 7/2001 | Niedospial, Jr. |
| D445,895 S | 7/2001 | Svendsen |
| 6,253,804 B1 | 7/2001 | Safabash |
| 6,258,078 B1 | 7/2001 | Thilly |
| 6,280,430 B1 | 8/2001 | Neftel et al. |
| 6,290,688 B1 | 9/2001 | Lopez et al. |

(56) References Cited

U.S. PATENT DOCUMENTS

| | | |
|---|---|---|
| 6,296,621 B1 | 10/2001 | Masuda et al. |
| 6,299,131 B1 | 10/2001 | Ryan |
| 6,343,629 B1 | 2/2002 | Wessman et al. |
| 6,348,044 B1 | 2/2002 | Coletti et al. |
| 6,358,236 B1 | 3/2002 | DeFoggi et al. |
| 6,364,866 B1 | 4/2002 | Furr et al. |
| 6,378,576 B2 | 4/2002 | Thibault et al. |
| 6,378,714 B1 | 4/2002 | Jansen et al. |
| 6,379,340 B1 | 4/2002 | Zinger et al. |
| 6,382,442 B1 | 5/2002 | Thibault et al. |
| 6,386,397 B2 | 5/2002 | Brotspies et al. |
| 6,408,897 B1 | 6/2002 | Laurent et al. |
| 6,409,708 B1 | 6/2002 | Wessman |
| 6,440,107 B1 | 8/2002 | Trombley, III et al. |
| 6,453,949 B1 | 9/2002 | Chau |
| 6,453,956 B2 | 9/2002 | Safabash |
| 6,474,375 B2 | 11/2002 | Spero et al. |
| 6,478,788 B1 | 11/2002 | Aneas |
| D468,015 S | 12/2002 | Horppu |
| 6,499,617 B1 | 12/2002 | Niedospial, Jr. et al. |
| 6,503,240 B1 | 1/2003 | Niedospial, Jr. et al. |
| 6,503,244 B2 | 1/2003 | Hayman |
| 6,520,932 B2 | 2/2003 | Taylor |
| 6,524,278 B1 | 2/2003 | Campbell et al. |
| 6,524,295 B2 | 2/2003 | Daubert et al. |
| D472,316 S | 3/2003 | Douglas et al. |
| 6,530,903 B2 | 3/2003 | Wang et al. |
| 6,537,263 B1 | 3/2003 | Aneas |
| D472,630 S | 4/2003 | Douglas et al. |
| 6,544,246 B1 | 4/2003 | Niedospial, Jr. |
| 6,551,299 B2 | 4/2003 | Miyoshi et al. |
| 6,558,365 B2 | 5/2003 | Zinger et al. |
| 6,571,837 B2 | 6/2003 | Jansen et al. |
| 6,572,591 B2 | 6/2003 | Mayer |
| 6,575,955 B2 | 6/2003 | Azzolini |
| 6,581,593 B1 | 6/2003 | Rubin et al. |
| 6,582,415 B1 | 6/2003 | Fowles et al. |
| D476,731 S | 7/2003 | Cise et al. |
| 6,591,876 B2 | 7/2003 | Safabash |
| 6,599,273 B1 | 7/2003 | Lopez |
| 6,601,721 B2 | 8/2003 | Jansen et al. |
| 6,626,309 B1 | 9/2003 | Jansen et al. |
| 6,638,244 B1 | 10/2003 | Reynolds |
| D482,121 S | 11/2003 | Harding et al. |
| D482,447 S | 11/2003 | Harding et al. |
| 6,651,956 B2 | 11/2003 | Miller |
| 6,652,509 B1 | 11/2003 | Helgren et al. |
| D483,487 S | 12/2003 | Harding et al. |
| D483,869 S | 12/2003 | Tran et al. |
| 6,656,433 B2 | 12/2003 | Sasso |
| 6,666,852 B2 | 12/2003 | Niedospial, Jr. |
| 6,681,810 B2 | 1/2004 | Weston |
| 6,681,946 B1 | 1/2004 | Jansen et al. |
| 6,682,509 B2 | 1/2004 | Lopez |
| 6,692,478 B1 | 2/2004 | Paradis |
| 6,692,829 B2 | 2/2004 | Stubler et al. |
| 6,695,829 B2 | 2/2004 | Hellstrom et al. |
| 6,699,229 B2 | 3/2004 | Zinger et al. |
| 6,706,022 B1 | 3/2004 | Leinsing et al. |
| 6,706,031 B2 | 3/2004 | Manera |
| 6,715,520 B2 | 4/2004 | Andreasson et al. |
| 6,729,370 B2 | 5/2004 | Norton et al. |
| 6,736,798 B2 | 5/2004 | Ohkubo et al. |
| 6,745,998 B2 | 6/2004 | Doyle |
| 6,746,438 B1 | 6/2004 | Arnissolle |
| 6,752,180 B2 | 6/2004 | Delay |
| D495,416 S | 8/2004 | Dimeo et al. |
| D496,457 S | 9/2004 | Prais et al. |
| 6,802,490 B2 | 10/2004 | Leinsing et al. |
| 6,832,994 B2 | 12/2004 | Niedospial, Jr. et al. |
| 6,852,103 B2 | 2/2005 | Fowles et al. |
| 6,875,203 B1 | 4/2005 | Fowles et al. |
| 6,875,205 B2 | 4/2005 | Leinsing |
| 6,878,131 B2 | 4/2005 | Novacek et al. |
| 6,890,328 B2 | 5/2005 | Fowles et al. |
| D506,256 S | 6/2005 | Miyoshi et al. |
| 6,901,975 B2 | 6/2005 | Aramata et al. |
| 6,945,417 B2 | 9/2005 | Jansen et al. |
| 6,948,522 B2 | 9/2005 | Newbrough et al. |
| 6,949,086 B2 | 9/2005 | Ferguson et al. |
| 6,951,613 B2 | 10/2005 | Reif et al. |
| 6,957,745 B2 | 10/2005 | Thibault et al. |
| RE38,996 E | 2/2006 | Crawford et al. |
| 6,994,315 B2 | 2/2006 | Ryan et al. |
| 6,997,916 B2 | 2/2006 | Simas, Jr. et al. |
| 6,997,917 B2 | 2/2006 | Niedospial, Jr. et al. |
| 7,024,968 B2 | 4/2006 | Raudabough et al. |
| 7,070,589 B2 | 7/2006 | Lolachi et al. |
| 7,074,216 B2 | 7/2006 | Fowles et al. |
| 7,083,600 B2 | 8/2006 | Meloul |
| 7,086,431 B2 | 8/2006 | D'Antonio et al. |
| 7,100,890 B2 | 9/2006 | Cote, Sr. et al. |
| 7,140,401 B2 | 11/2006 | Wilcox et al. |
| 7,150,735 B2 | 12/2006 | Hickle |
| 7,192,423 B2 | 3/2007 | Wong |
| 7,195,623 B2 | 3/2007 | Burroughs et al. |
| 7,241,285 B1 | 7/2007 | Dikeman |
| 7,294,122 B2 | 11/2007 | Kubo et al. |
| 7,306,199 B2 | 12/2007 | Leinsing et al. |
| D561,348 S | 2/2008 | Zinger et al. |
| 7,326,188 B1 | 2/2008 | Russell et al. |
| 7,326,194 B2 | 2/2008 | Zinger et al. |
| 7,350,764 B2 | 4/2008 | Raybuck |
| 7,354,422 B2 | 4/2008 | Riesenberger et al. |
| 7,354,427 B2 | 4/2008 | Fangrow |
| 7,425,209 B2 | 9/2008 | Fowles et al. |
| 7,435,246 B2 | 10/2008 | Zihlmann |
| 7,452,348 B2 | 11/2008 | Hasegawa |
| 7,470,257 B2 | 12/2008 | Norton et al. |
| 7,470,265 B2 | 12/2008 | Brugger et al. |
| 7,472,932 B2 | 1/2009 | Weber et al. |
| 7,488,297 B2 | 2/2009 | Flaherty |
| 7,491,197 B2 | 2/2009 | Jansen et al. |
| 7,497,848 B2 | 3/2009 | Leinsing et al. |
| 7,523,967 B2 | 4/2009 | Steppe |
| 7,530,546 B2 | 5/2009 | Ryan et al. |
| D595,420 S | 6/2009 | Suzuki et al. |
| D595,421 S | 6/2009 | Suzuki et al. |
| 7,540,863 B2 | 6/2009 | Haindl |
| 7,540,865 B2 | 6/2009 | Griffin et al. |
| 7,544,191 B2 | 6/2009 | Peluso et al. |
| D595,862 S | 7/2009 | Suzuki et al. |
| D595,863 S | 7/2009 | Suzuki et al. |
| 7,611,487 B2 | 11/2009 | Woehr et al. |
| 7,611,502 B2 | 11/2009 | Daly |
| 7,615,041 B2 | 11/2009 | Sullivan et al. |
| 7,628,779 B2 | 12/2009 | Aneas |
| 7,632,261 B2 | 12/2009 | Zinger et al. |
| D608,900 S | 1/2010 | Giraud et al. |
| 7,654,995 B2 | 2/2010 | Warren et al. |
| 7,670,326 B2 | 3/2010 | Shemesh |
| 7,695,445 B2 | 4/2010 | Yuki |
| D616,090 S | 5/2010 | Kawamura |
| 7,713,247 B2 | 5/2010 | Lopez |
| 7,717,886 B2 | 5/2010 | Lopez |
| 7,722,090 B2 | 5/2010 | Burton et al. |
| D616,984 S | 6/2010 | Gilboa |
| 7,731,678 B2 | 6/2010 | Tennican et al. |
| 7,743,799 B2 | 6/2010 | Mosler et al. |
| 7,744,581 B2 | 6/2010 | Wallen et al. |
| 7,757,901 B2 | 7/2010 | Welp |
| 7,758,082 B2 | 7/2010 | Weigel et al. |
| 7,762,524 B2 | 7/2010 | Cawthon et al. |
| 7,766,304 B2 | 8/2010 | Phillips |
| 7,771,383 B2 | 8/2010 | Truitt et al. |
| D624,641 S | 9/2010 | Boclet |
| 7,799,009 B2 | 9/2010 | Niedospial, Jr. et al. |
| 7,803,140 B2 | 9/2010 | Fangrow, Jr. |
| D627,216 S | 11/2010 | Fulginiti |
| D630,732 S | 1/2011 | Lev et al. |
| 7,862,537 B2 | 1/2011 | Zinger et al. |
| 7,867,215 B2 | 1/2011 | Akerlund et al. |
| 7,879,018 B2 | 2/2011 | Zinger et al. |
| D634,007 S | 3/2011 | Zinger et al. |

(56) References Cited

U.S. PATENT DOCUMENTS

| | | |
|---|---|---|
| 7,900,659 B2 | 3/2011 | Whitley et al. |
| D637,713 S | 5/2011 | Nord et al. |
| 7,985,216 B2 | 7/2011 | Daily et al. |
| D644,104 S | 8/2011 | Maeda et al. |
| 7,993,328 B2 | 8/2011 | Whitley |
| 8,007,461 B2 | 8/2011 | Huo et al. |
| 8,012,132 B2 | 9/2011 | Lum et al. |
| 8,016,809 B2 | 9/2011 | Zinger et al. |
| 8,021,325 B2 | 9/2011 | Zinger et al. |
| 8,025,653 B2 | 9/2011 | Capitaine et al. |
| 8,029,472 B2 | 10/2011 | Leinsing et al. |
| 8,038,123 B2 | 10/2011 | Ruschke et al. |
| 8,066,688 B2 | 11/2011 | Zinger et al. |
| 8,070,739 B2 | 12/2011 | Zinger et al. |
| 8,075,550 B2 | 12/2011 | Nord et al. |
| 8,096,525 B2 | 1/2012 | Ryan |
| 8,105,314 B2 | 1/2012 | Fangrow, Jr. |
| D654,166 S | 2/2012 | Lair |
| D655,017 S | 2/2012 | Mosler et al. |
| 8,122,923 B2 | 2/2012 | Kraus et al. |
| 8,123,736 B2 | 2/2012 | Kraushaar et al. |
| D655,071 S | 3/2012 | Davila |
| 8,157,784 B2 | 4/2012 | Rogers |
| 8,167,863 B2 | 5/2012 | Yow |
| 8,172,824 B2 | 5/2012 | Pfeifer et al. |
| 8,177,768 B2 | 5/2012 | Leinsing |
| 8,182,452 B2 | 5/2012 | Mansour et al. |
| 8,187,248 B2 | 5/2012 | Zihlmann |
| 8,196,614 B2 | 6/2012 | Kriheli |
| 8,197,459 B2 | 6/2012 | Jansen et al. |
| 8,211,069 B2 | 7/2012 | Fangrow, Jr. |
| 8,225,959 B2 | 7/2012 | Lambrecht |
| 8,241,268 B2 | 8/2012 | Whitley |
| 8,262,628 B2 | 9/2012 | Fangrow, Jr. |
| 8,262,641 B2 | 9/2012 | Vedrine et al. |
| 8,267,127 B2 | 9/2012 | Kriheli |
| D669,980 S | 10/2012 | Lev et al. |
| 8,287,513 B2 | 10/2012 | Ellstrom et al. |
| D673,673 S | 1/2013 | Wang |
| D674,088 S | 1/2013 | Lev et al. |
| D681,230 S | 4/2013 | Mosler et al. |
| 8,454,573 B2 | 6/2013 | Wyatt et al. |
| 8,469,939 B2 | 6/2013 | Fangrow, Jr. |
| 8,475,404 B2 | 7/2013 | Foshee et al. |
| 8,480,645 B1 | 7/2013 | Choudhury et al. |
| 8,480,646 B2 | 7/2013 | Nord et al. |
| 8,506,548 B2 | 8/2013 | Okiyama |
| 8,511,352 B2 | 8/2013 | Kraus et al. |
| 8,512,309 B2 | 8/2013 | Shemesh et al. |
| D690,418 S | 9/2013 | Rosenquist |
| 8,523,837 B2 | 9/2013 | Wiggins et al. |
| 8,545,476 B2 | 10/2013 | Ariagno et al. |
| 8,551,067 B2 | 10/2013 | Zinger et al. |
| 8,556,879 B2 | 10/2013 | Okiyama |
| 8,562,582 B2 | 10/2013 | Tuckwell et al. |
| 8,608,723 B2 | 12/2013 | Lev et al. |
| 8,628,508 B2 | 1/2014 | Weitzel et al. |
| 8,684,992 B2 | 4/2014 | Sullivan et al. |
| 8,684,994 B2 | 4/2014 | Lev et al. |
| D717,406 S | 11/2014 | Stanley et al. |
| 8,900,212 B2 | 12/2014 | Kubo |
| 2001/0000347 A1 | 4/2001 | Hellstrom et al. |
| 2001/0025671 A1 | 10/2001 | Safabash |
| 2001/0029360 A1 | 10/2001 | Miyoshi et al. |
| 2001/0051793 A1 | 12/2001 | Weston |
| 2002/0017328 A1 | 2/2002 | Loo |
| 2002/0066715 A1 | 6/2002 | Niedospial |
| 2002/0087118 A1 | 7/2002 | Reynolds et al. |
| 2002/0087141 A1 | 7/2002 | Zinger et al. |
| 2002/0087144 A1 | 7/2002 | Zinger et al. |
| 2002/0121496 A1 | 9/2002 | Thiebault et al. |
| 2002/0123736 A1 | 9/2002 | Fowles et al. |
| 2002/0127150 A1 | 9/2002 | Sasso |
| 2002/0128628 A1 | 9/2002 | Fathallah |
| 2002/0138045 A1 | 9/2002 | Moen |
| 2002/0173752 A1 | 11/2002 | Polzin |
| 2002/0193777 A1 | 12/2002 | Aneas |
| 2003/0028156 A1 | 2/2003 | Juliar |
| 2003/0036725 A1 | 2/2003 | Lavi et al. |
| 2003/0068354 A1 | 4/2003 | Reif et al. |
| 2003/0073971 A1 | 4/2003 | Saker |
| 2003/0100866 A1 | 5/2003 | Reynolds |
| 2003/0109846 A1 | 6/2003 | Zinger et al. |
| 2003/0120209 A1 | 6/2003 | Jensen et al. |
| 2003/0153895 A1 | 8/2003 | Leinsing |
| 2003/0187420 A1 | 10/2003 | Akerlund et al. |
| 2003/0191445 A1 | 10/2003 | Wallen et al. |
| 2003/0195479 A1 | 10/2003 | Kuracina et al. |
| 2003/0199846 A1 | 10/2003 | Fowles et al. |
| 2003/0199847 A1 | 10/2003 | Akerlund et al. |
| 2004/0024354 A1 | 2/2004 | Reynolds |
| 2004/0039365 A1 | 2/2004 | Aramata et al. |
| 2004/0044327 A1 | 3/2004 | Hasegawa |
| 2004/0073189 A1 | 4/2004 | Wyatt et al. |
| 2004/0143226 A1 | 7/2004 | Marsden |
| 2004/0153047 A1 | 8/2004 | Blank et al. |
| 2004/0181192 A1 | 9/2004 | Cuppy |
| 2004/0204699 A1 | 10/2004 | Hanly et al. |
| 2004/0217315 A1 | 11/2004 | Doyle |
| 2004/0225274 A1 | 11/2004 | Jansen et al. |
| 2004/0236305 A1 | 11/2004 | Jansen et al. |
| 2004/0255952 A1 | 12/2004 | Carlsen et al. |
| 2005/0015070 A1 | 1/2005 | Delnevo et al. |
| 2005/0016626 A1 | 1/2005 | Wilcox et al. |
| 2005/0055008 A1 | 3/2005 | Paradis et al. |
| 2005/0082828 A1 | 4/2005 | Wicks et al. |
| 2005/0124964 A1 | 6/2005 | Niedospial et al. |
| 2005/0137566 A1 | 6/2005 | Fowles et al. |
| 2005/0148994 A1 | 7/2005 | Leinsing |
| 2005/0159724 A1 | 7/2005 | Enerson |
| 2005/0182383 A1 | 8/2005 | Wallen |
| 2005/0209554 A1 | 9/2005 | Landau |
| 2005/0261637 A1 | 11/2005 | Miller |
| 2005/0277896 A1 | 12/2005 | Messerli et al. |
| 2006/0030832 A1 | 2/2006 | Niedospial et al. |
| 2006/0079834 A1 | 4/2006 | Tennican et al. |
| 2006/0089594 A1 | 4/2006 | Landau |
| 2006/0089603 A1 | 4/2006 | Truitt et al. |
| 2006/0095015 A1 | 5/2006 | Hobbs et al. |
| 2006/0106360 A1 | 5/2006 | Wong |
| 2006/0135948 A1 | 6/2006 | Varma |
| 2006/0155257 A1 | 7/2006 | Reynolds |
| 2006/0253084 A1 | 11/2006 | Nordgren |
| 2007/0024995 A1 | 2/2007 | Hayashi |
| 2007/0060904 A1 | 3/2007 | Vedrine et al. |
| 2007/0079894 A1* | 4/2007 | Kraus ................ A61J 1/2089 141/319 |
| 2007/0083164 A1 | 4/2007 | Barrelle et al. |
| 2007/0088252 A1 | 4/2007 | Pestotnik et al. |
| 2007/0088293 A1 | 4/2007 | Fangrow |
| 2007/0088313 A1 | 4/2007 | Zinger et al. |
| 2007/0106244 A1 | 5/2007 | Mosler et al. |
| 2007/0112324 A1 | 5/2007 | Hamedi-Sangsari |
| 2007/0156112 A1 | 7/2007 | Walsh |
| 2007/0167904 A1 | 7/2007 | Zinger et al. |
| 2007/0191760 A1 | 8/2007 | Iguchi et al. |
| 2007/0191764 A1 | 8/2007 | Zihlmann |
| 2007/0191767 A1 | 8/2007 | Hennessy et al. |
| 2007/0203451 A1 | 8/2007 | Murakami et al. |
| 2007/0219483 A1 | 9/2007 | Kitani et al. |
| 2007/0244447 A1 | 10/2007 | Capitaine et al. |
| 2007/0244461 A1 | 10/2007 | Fangrow |
| 2007/0244462 A1 | 10/2007 | Fangrow |
| 2007/0244463 A1 | 10/2007 | Warren et al. |
| 2007/0249995 A1 | 10/2007 | Van Manen |
| 2007/0255202 A1 | 11/2007 | Kitani et al. |
| 2007/0265574 A1 | 11/2007 | Tennican et al. |
| 2007/0265581 A1 | 11/2007 | Funamura et al. |
| 2007/0270778 A9 | 11/2007 | Zinger et al. |
| 2007/0287953 A1 | 12/2007 | Ziv et al. |
| 2007/0299404 A1 | 12/2007 | Katoh et al. |
| 2008/0009789 A1 | 1/2008 | Zinger et al. |
| 2008/0009822 A1 | 1/2008 | Enerson |
| 2008/0135051 A1 | 6/2008 | Lee |

(56) References Cited

U.S. PATENT DOCUMENTS

| | | |
|---|---|---|
| 2008/0172024 A1 | 7/2008 | Yow |
| 2008/0188799 A1 | 8/2008 | Mueller-Beckhaus et al. |
| 2008/0249479 A1 | 10/2008 | Zinger et al. |
| 2008/0249498 A1 | 10/2008 | Fangrow |
| 2008/0262465 A1 | 10/2008 | Zinger et al. |
| 2008/0287905 A1 | 11/2008 | Hiejima et al. |
| 2008/0294100 A1 | 11/2008 | de Costa et al. |
| 2008/0306439 A1 | 12/2008 | Nelson et al. |
| 2008/0312634 A1 | 12/2008 | Helmerson et al. |
| 2009/0012492 A1 | 1/2009 | Zihlmann |
| 2009/0082750 A1* | 3/2009 | Denenburg ........... A61J 1/2089 604/407 |
| 2009/0143758 A1 | 6/2009 | Okiyama |
| 2009/0177177 A1 | 7/2009 | Zinger et al. |
| 2009/0177178 A1 | 7/2009 | Pedersen |
| 2009/0187140 A1 | 7/2009 | Racz |
| 2009/0216212 A1 | 8/2009 | Fangrow, Jr. |
| 2009/0267011 A1 | 10/2009 | Hatton et al. |
| 2009/0299325 A1 | 12/2009 | Vedrine et al. |
| 2009/0326506 A1 | 12/2009 | Hasegawa et al. |
| 2010/0010443 A1 | 1/2010 | Morgan et al. |
| 2010/0022985 A1 | 1/2010 | Sullivan et al. |
| 2010/0030181 A1 | 2/2010 | Helle et al. |
| 2010/0036319 A1 | 2/2010 | Drake et al. |
| 2010/0076397 A1 | 3/2010 | Reed et al. |
| 2010/0087786 A1 | 4/2010 | Zinger et al. |
| 2010/0137827 A1 | 6/2010 | Warren et al. |
| 2010/0160889 A1 | 6/2010 | Smith et al. |
| 2010/0168712 A1 | 7/2010 | Tuckwell et al. |
| 2010/0179506 A1 | 7/2010 | Shemesh et al. |
| 2010/0198148 A1 | 8/2010 | Zinger et al. |
| 2010/0204670 A1 | 8/2010 | Kraushaar et al. |
| 2010/0241088 A1 | 9/2010 | Ranalletta et al. |
| 2010/0274184 A1 | 10/2010 | Chun |
| 2010/0286661 A1 | 11/2010 | Raday et al. |
| 2010/0312220 A1 | 12/2010 | Kalitzki |
| 2011/0004184 A1 | 1/2011 | Proksch et al. |
| 2011/0054440 A1 | 3/2011 | Lewis |
| 2011/0087164 A1 | 4/2011 | Mosler et al. |
| 2011/0160701 A1 | 6/2011 | Wyatt et al. |
| 2011/0175347 A1 | 7/2011 | Okiyama |
| 2011/0218511 A1 | 9/2011 | Yokoyama |
| 2011/0224640 A1 | 9/2011 | Kuhn et al. |
| 2011/0230856 A1 | 9/2011 | Kyle et al. |
| 2011/0264037 A1 | 10/2011 | Foshee et al. |
| 2011/0264069 A1 | 10/2011 | Bochenko |
| 2011/0276007 A1 | 11/2011 | Denenburg |
| 2011/0319827 A1 | 12/2011 | Leinsing et al. |
| 2012/0022469 A1 | 1/2012 | Alpert |
| 2012/0053555 A1 | 3/2012 | Ariagno et al. |
| 2012/0059346 A1 | 3/2012 | Sheppard et al. |
| 2012/0067429 A1 | 3/2012 | Mosler et al. |
| 2012/0078214 A1 | 3/2012 | Finke et al. |
| 2012/0123382 A1 | 5/2012 | Kubo |
| 2012/0184938 A1 | 7/2012 | Lev et al. |
| 2012/0215182 A1 | 8/2012 | Mansour et al. |
| 2012/0220977 A1 | 8/2012 | Yow |
| 2012/0220978 A1 | 8/2012 | Lev et al. |
| 2012/0265163 A1 | 10/2012 | Cheng et al. |
| 2012/0271229 A1 | 10/2012 | Lev et al. |
| 2012/0296307 A1 | 11/2012 | Holt et al. |
| 2012/0310203 A1 | 12/2012 | Khaled et al. |
| 2012/0323187 A1 | 12/2012 | Iwase et al. |
| 2012/0323210 A1 | 12/2012 | Lev et al. |
| 2013/0053814 A1 | 2/2013 | Mueller-Beckhaus et al. |
| 2013/0096493 A1 | 4/2013 | Kubo et al. |
| 2013/0144248 A1 | 6/2013 | Putter et al. |
| 2013/0199669 A1 | 8/2013 | Moy et al. |
| 2013/0226100 A1* | 8/2013 | Lev .................... A61J 1/2096 604/246 |
| 2013/0231630 A1 | 9/2013 | Kraus et al. |
| 2013/0237904 A1 | 9/2013 | Deneburg et al. |
| 2013/0289530 A1 | 10/2013 | Wyatt et al. |
| 2014/0020793 A1* | 1/2014 | Denenburg ........... A61J 1/2089 141/329 |
| 2014/0096862 A1 | 4/2014 | Aneas |
| 2014/0150911 A1 | 6/2014 | Hanner et al. |

FOREIGN PATENT DOCUMENTS

| | | |
|---|---|---|
| DE | 4122476 A1 | 1/1993 |
| DE | 19504413 A1 | 8/1996 |
| DE | 202004012714 U1 | 11/2004 |
| DE | 202009011019 U1 | 12/2010 |
| EP | 0192661 A1 | 9/1986 |
| EP | 0195018 A1 | 9/1986 |
| EP | 0258913 A2 | 3/1988 |
| EP | 0416454 A2 | 3/1991 |
| EP | 0518397 A1 | 12/1992 |
| EP | 0521460 A1 | 1/1993 |
| EP | 0637443 A1 | 2/1995 |
| EP | 0737467 A1 | 10/1996 |
| EP | 761562 A1 | 3/1997 |
| EP | 765652 A1 | 4/1997 |
| EP | 765853 A1 | 4/1997 |
| EP | 0806597 A1 | 11/1997 |
| EP | 0814866 A1 | 1/1998 |
| EP | 829248 A2 | 3/1998 |
| EP | 0856331 A2 | 8/1998 |
| EP | 882441 A2 | 12/1998 |
| EP | 0887085 A2 | 12/1998 |
| EP | 0887885 A2 | 12/1998 |
| EP | 897708 A2 | 2/1999 |
| EP | 0898951 A2 | 3/1999 |
| EP | 960616 A2 | 12/1999 |
| EP | 1008337 A1 | 6/2000 |
| EP | 1029526 A1 | 8/2000 |
| EP | 1034809 A1 | 9/2000 |
| EP | 1051988 A2 | 11/2000 |
| EP | 1323403 A1 | 7/2003 |
| EP | 1329210 A1 | 7/2003 |
| EP | 1396250 A1 | 3/2004 |
| EP | 1454609 A1 | 9/2004 |
| EP | 1454650 A1 | 9/2004 |
| EP | 1498097 A2 | 1/2005 |
| EP | 1872824 A1 | 1/2008 |
| EP | 1911432 A1 | 4/2008 |
| EP | 1919432 A1 | 5/2008 |
| EP | 1930038 A2 | 6/2008 |
| EP | 2090278 A1 | 8/2009 |
| EP | 2351548 A1 | 8/2011 |
| EP | 2351549 A1 | 8/2011 |
| EP | 2462913 A1 | 6/2012 |
| FR | 2029242 A5 | 10/1970 |
| FR | 2856660 A1 | 12/2004 |
| FR | 2869795 A1 | 11/2005 |
| FR | 2931363 A1 | 11/2009 |
| GB | 1444210 A | 7/1976 |
| IL | 171662 | 10/2005 |
| JP | 03-062426 B | 9/1991 |
| JP | 4329954 A | 11/1992 |
| JP | 06-050656 U | 7/1994 |
| JP | H08-000710 A | 1/1996 |
| JP | 09-104460 A | 4/1997 |
| JP | 09-104461 A | 4/1997 |
| JP | 10-118158 A | 5/1998 |
| JP | H10-504736 A | 5/1998 |
| JP | 11503627 T | 3/1999 |
| JP | 11-319031 A | 11/1999 |
| JP | 2000-508934 A | 7/2000 |
| JP | 2000-237278 A | 9/2000 |
| JP | 2001-505083 A | 4/2001 |
| JP | 2002-035140 A | 2/2002 |
| JP | 2002-516160 A | 6/2002 |
| JP | 2002-355318 A | 12/2002 |
| JP | 2003-033441 A | 2/2003 |
| JP | 2003-102807 A | 4/2003 |
| JP | 2004-097253 A | 4/2004 |
| JP | 2004-522541 A | 7/2004 |
| JP | 2010-179128 A | 8/2010 |
| WO | 8601712 A1 | 3/1986 |
| WO | 9003536 A1 | 4/1990 |

(56) References Cited

FOREIGN PATENT DOCUMENTS

| | | | |
|---|---|---|---|
| WO | 9403373 | A1 | 2/1994 |
| WO | 9507066 | A1 | 3/1995 |
| WO | 9600053 | A1 | 1/1996 |
| WO | 9629113 | A1 | 9/1996 |
| WO | 9736636 | A1 | 10/1997 |
| WO | 9832411 | A1 | 7/1998 |
| WO | 9837854 | A1 | 9/1998 |
| WO | 9961093 | A1 | 12/1999 |
| WO | 0128490 | A1 | 4/2001 |
| WO | 0130425 | A1 | 5/2001 |
| WO | 0132524 | A1 | 5/2001 |
| WO | 0160311 | A1 | 8/2001 |
| WO | 0191693 | A2 | 12/2001 |
| WO | 0209797 | A1 | 2/2002 |
| WO | 0232372 | A1 | 4/2002 |
| WO | 0236191 | A2 | 5/2002 |
| WO | 02066100 | A2 | 8/2002 |
| WO | 02089900 | A1 | 11/2002 |
| WO | 03051423 | A2 | 6/2003 |
| WO | 03070147 | A2 | 8/2003 |
| WO | 03079956 | A1 | 10/2003 |
| WO | 2004041148 | A1 | 5/2004 |
| WO | 2005002492 | A1 | 1/2005 |
| WO | 2005041846 | A2 | 5/2005 |
| WO | 2005105014 | A2 | 11/2005 |
| WO | 2006099441 | A2 | 9/2006 |
| WO | 2007015233 | A1 | 2/2007 |
| WO | 2007017868 | A1 | 2/2007 |
| WO | 2007052252 | A1 | 5/2007 |
| WO | 2007101772 | A1 | 9/2007 |
| WO | 2007105221 | A1 | 9/2007 |
| WO | 2008081424 | A2 | 7/2008 |
| WO | 2008126090 | A1 | 10/2008 |
| WO | 2009026443 | A2 | 2/2009 |
| WO | 2009029010 | A1 | 3/2009 |
| WO | 2009038860 | A2 | 3/2009 |
| WO | 2009040804 | A2 | 4/2009 |
| WO | 2009087572 | A1 | 7/2009 |
| WO | 2009093249 | A1 | 7/2009 |
| WO | 2009112489 | A1 | 9/2009 |
| WO | 2009146088 | A1 | 12/2009 |
| WO | 2010061743 | A1 | 6/2010 |
| WO | 2010117580 | A1 | 10/2010 |
| WO | 2011039747 | A1 | 4/2011 |
| WO | 2011058545 | A1 | 5/2011 |
| WO | 2011058548 | A1 | 5/2011 |
| WO | 2011077434 | A1 | 6/2011 |
| WO | 2011104711 | A1 | 9/2011 |
| WO | 2012063230 | A1 | 5/2012 |
| WO | 2012143921 | A1 | 10/2012 |
| WO | 2013127813 | A1 | 9/2013 |
| WO | 2013134246 | A1 | 9/2013 |
| WO | 2013156944 | A1 | 10/2013 |
| WO | 2014033706 | A2 | 3/2014 |
| WO | 2014033710 | A1 | 3/2014 |

OTHER PUBLICATIONS

Office Action issued Jul. 31, 2014 in U.S. Appl. No. 29/438,141 by Gilboa.
U.S. Appl. No. 29/502,037 by LEV, filed Sep. 11, 2014.
U.S. Appl. No. 29/502,053 by LEV, filed Sep. 11, 2014.
Office Action issued Mar. 6, 2012 in U.S. Appl. No. 12/678,928.
Int'l Search Report issued Feb. 3, 2011 in Int'l Application No. PCT/IL2010/000777; Written Opinion.
Int'l Search Report issued Mar. 17, 2011 in Int'l Application No. PCT/IL2010/000854; Written Opinion.
Int'l Search Report issued Mar. 17, 2011 in Int'l Application No. PCT/IL2010/000915; Written Opinion.
U.S. Appl. No. 13/505,790 by Lev, filed May 3, 2012.
U.S. Appl. No. 13/505,881 by Lev, filed May 3, 2012.
U.S. Appl. No. 13/522,410 by Lev, filed Jul. 16, 2012.
U.S. Appl. No. 13/576,461 by Lev, filed Aug. 1, 2012.
Office Action issued Jun. 14, 2012 in U.S. Appl. No. 29/376,980.
Office Action issued Jun. 15, 2012 in U.S. Appl. No. 29/413,170.
Office Action issued Jun. 21, 2012 in U.S. Appl. No. 12/596,167.
Alaris Medical Systems Product Brochure, 4 pages, Issue 1, Oct. 11, 1999.
Smart Site Needle-Free Systems, Alaris Medical Systems Webpage, 4 pages, Feb. 2006.
Photographs of Alaris Medical Systems SmartSite.RTM. device, 5 pages, 2002.
Non-Vented Vial Access Pin with ULTRASITE.RTM. Valve, B. Braun Medical, Inc. website and product description, 3 pages, Feb. 2006.
Int'l Search Report issued Aug. 16, 2012 in Int'l Application No. PCT/IL2012/000164.
U.S. Appl. No. 29/438,134 by Lev, filed Nov. 27, 2012.
U.S. Appl. No. 29/438,141 by Gilboa, filed Nov. 27, 2012.
Int'l Search Report issued Jan. 22, 2013 in Int'l Application No. PCT/IL2012/000354.
Int'l Search Report issued Mar. 18, 2013 in Int'l Application No. PCT/IL2012/050516.
Office Action issued Apr. 2, 2013 in U.S. Appl. No. 13/505,790.
Int'l Search Report and Written Opinion issued Mar. 6, 2012 in Int'l Application No. PCT/IL2011/000834.
U.S. Appl. No. 13/883,289 by Lev, filed May 3, 2013.
Int'l Search Report & Written Opinion issued on Mar. 7, 2012 in Int'l Application No. PCT/IL2011/000829.
U.S. Appl. No. 13/884,981 by Denenburg, filed May 13, 2013.
Office Action issued May 31, 2013 in U.S. Appl. No. 13/505,790.
Int'l Search Report issued Jun. 5, 2013 in Int'l Application No. PCT/IL2012/050407.
Int'l Search Report issued Jun. 19, 2013 in Int'l Application No. PCT/IL2013/050167.
Int'l Search Report issued Jul. 1, 2013 in Int'l Application No. PCT/IL2013/050180.
Int'l Search Report issued Jul. 31, 2013 in Int'l Application No. PCT/IL2013/050313.
Int'l Search Report issued Jul. 26, 2013 in Int'l Application No. PCT/IL2013/050316.
English translation of an Office Action issued Jun. 19, 2013 in JP Application No. 2012-531551.
Office Action issued Aug. 20, 2013 in U.S. Appl. No. 13/576,461 by Lev.
Int'l Preliminary Report on Patentability issued Aug. 28, 2012 in Int'l Application No. PCT/IL2011/000186.
U.S. Appl. No. 14/005,751 by Denenburg, filed Sep. 17, 2013.
English translation of an Office Action issued Jul. 26, 2013 in JP Application No. 2012-538464.
International Search Report Issued Jan. 23, 2007 in Int'l Application No. PCT/IL/2006/001228.
IV disposables sets catalogue, Cardinal Health, Alaris® products, SmartSite® access devices and accessories product No. 10013365, SmartSite add-on bag access device with spike adapter and needle-free valve bag access port, pp. 1-5, Fall edition (2007).
Drug Administration Systems product information sheets; http://www.westpharma.com/eu/en/products/Pages/Vial2Bag.aspx; pp. 1-3 (admitted prior art).
Office Action Issued Jun. 8, 2010 in U.S. Appl. No. 12/112,490 by Zinger.
Office Action issued Sep. 28, 2010 in U.S. Appl. No. 12/112,490 by Zinger.
Article with picture of West Pharmaceutical Services' Vial2Bag Needleless System, [on-line]; ISIPS Newsletter, Oct. 26, 2007]; retrieved from Internet Feb. 16, 2010]; URL:<http://www.isips.org/reports/ISIPS_Newsletter_October_26_2007.html.> (7 pages. see pp. 5-6).
Office Action issued Jun. 15, 2011 in JP Application No. 2008-538492.
Translation of Office Action issued Jun. 18, 2012 in JP Application No. 2008-538492.
Translation of Office Action issued Apr. 15, 2013 in JP Application No. 2008-538492.
Office Action issued Jul. 13, 2012 in U.S. Appl. No. 12/112,490 by Zinger.

(56) References Cited

OTHER PUBLICATIONS

Office Action issued Jan. 23, 2013 in U.S. Appl. No. 12/112,490 by Zinger.
Int'l Preliminary Report on Patentability issued May 6, 2008 in Int'l Application No. PCT/IL2006/001228.
Written Opinion issued Aug. 16, 2012 in Int'l Application No. PCT/IL2012/000164.
English translation of an Office Action issued Sep. 10, 2013 in JP Application No. 2012-554468.
Office Action issued Nov. 11, 2013 in IL Application No. 218730.
U.S. Appl. No. 29/478,723 by Lev, filed Jan. 8, 2014.
U.S. Appl. No. 29/478,726 by Lev, filed Jan. 8, 2014.
Office Action issued Jan. 2, 2014 in U.S. Appl. No. 13/505,881 by Lev.
Int'l Preliminary Report on Patentability issued Sep. 24, 2013 in Int'l Application No. PCT/IL2012/000354.
Office Action issued Feb. 13, 2014 in U.S. Appl. No. 13/884,981 by Denenburg.
U.S. Appl. No. 14/345,094 by Lev, filed Mar. 14, 2014.
Int'l Search Report and Written Opinion issued Jan. 7, 2014 in Int'l Application No. PCT/IL2012/050721.
English translation of an Office Action issued Jan. 9, 2014 in JP Application No. 2010-526421.
English translation of an Office Action issued Dec. 4, 2013 in CN Application No. 201080051210.3.
English translation of an Office Action issued Dec. 25, 2013 in CN Application No. 201180006530.1.
Office Action issued Nov. 28, 2013 in in Application No. 4348/DELNP/2008.
Office Action issued Oct. 8, 2013 in CN Application No. 201080043825.1.
English translation of an Office Action issued Feb. 4, 2014 in JP Application No. 2012-554468.
Office Action issued Jan. 17, 2014 in CN Application No. 201180006534.X.
Int'l Search Report and Written Opinion issued May 8, 2014 in Int'l Application No. PCT/IL2013/050706.
English translation of an Office Action issued Apr. 28, 2014 in JP Application No. 2013-537257.
Int'l Preliminary Report on Patentability issued Jan. 14, 2014 in Int'l Application No. PCT/IL2012/050516.
Office Action issued May 6, 2014 in U.S. Appl. No. 13/505,881 by Lev.
U.S. Appl. No. 14/366,306 by Lev, filed Jun. 18, 2014.
Office Action issued Apr. 17, 2014 in CN Application No. 201080051201.4.
Int'l Search Report and Written Opinion issued Jul. 16, 2014 in Int'l Application No. PCT/IL2014/050327.
English translation of an Office Action issued Jun. 30, 2014 in CN Application No. 201180052962.6.
Extended European Search Report issued Jun. 3, 2014 in EP Application No. 08781828.2.
Written Opinion issued Jul. 1, 2013 in Int'l Application No. PCT/IL2013/050180.
Int'l Preliminary Report on Patentability issued Apr. 1, 2014 in Int'l Application No. PCT/IL2013/050180.
Written Opinion issued Jul. 31, 2013 in Int'l Application No. PCT/IL2013/050313.
U.S. Appl. No. 14/391,792 by Lev, filed Oct. 10, 2014.
U.S. Appl. No. 14/504,979 by Lev, filed Oct. 2, 2014.
Int'l Search Report and Written Opinion issued Sep. 2, 2014 in Int'l Application No. PCT/IL2014/050405.
Int'l Search Report and Written Opinion issued Oct. 17, 2014 in Int'l Application No. PCT/IL2014/050680.
English translation of an Office Action issued Aug. 28, 2014 in JP Application No. 2013-168885.
Written Opinion issued Jun. 5, 2013 in Int'l Application No. PCT/IL2012/050407.
Int'l Preliminary Report on Patentability issued Aug. 20, 2014 in Int'l Application No. PCT/IL2012/050407.
Office Action issued Jan. 2, 2015 in U.S. Appl. No. 29/438,141 by Gilboa.
Office Action issued Jan. 5, 2015 in U.S. Appl. No. 29/413,220 by Lev.
Office Action issued Jan. 7, 2015 in U.S. Appl. No. 29/438,134 by Lev.
U.S. Appl. No. 14/423,595 by Lev, filed Feb. 24, 2015.
U.S. Appl. No. 14/423,612 by Lev, filed Feb. 24, 2015.
U.S. Appl. No. 14/425,582 by Lev, filed Mar. 3, 2015.
Office Action issued Mar. 17, 2015 in U.S. Appl. No. 14/504,979 by Lev.
Office Action issued Apr. 9, 2015 in U.S. Appl. No. 13/883,289 by Lev.
Office Action issued May 28, 2015 in U.S. Appl. No. 14/391,792 by Lev.
Written Opinion issued Apr. 10, 2015 in Int'l Application No. PCT/IL2014/050405.
Response to Written Opinion dated Mar. 9, 2015 in Int'l Application No. PCT/IL2014/050405.
Int'l Preliminary Report on Patentability issued Aug. 24, 2015 in Int'l Application No. PCT/IL2014/050405.
U.S. Appl. No. 14/888,590 by Marks, filed Nov. 2, 2015.
U.S. Appl. No. 14/784,300 by Lev, filed Oct. 14, 2015.
U.S. Appl. No. 29/544,969 by Ben Shalom, filed Nov. 9, 2015.
Office Action issued Aug. 24, 2015 in U.S. Appl. No. 14/366,306 by Lev.
Office Action issued Mar. 10, 2015 in EP Application No. 12 812 395.7.
Office Action issued Aug. 7, 2015 in JP Application No. 2015-529206.
Grifols Vial Adapter Product Literature, 2 pages, Jan. 2002.
Novel Transfer, Mixing and Drug Delivery Systems, MOP Medimop Medical Projects Ltd. Catalog, 4 pages, Rev. 4, 2004.
Office Action Issued Oct. 6, 2003 in U.S. Appl. No. 10/062,796.
Office Action Issued Feb. 22, 2005 in U.S. Appl. No. 10/062,796.
Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
http://www.westpharma.com/en/products/Pages/Mixject.aspx (admitted prior art), [Retrieved on Aug. 8, 2012].
http://www.westpharma.com/SiteCollectionDocuments/Recon/mixject%20product%20sheet.pdf; MIXJECT product information sheet pp. 1. (admitted prior art), [Publicly available prior to Apr. 5, 2011].
Int'l Search Report Issued Jul. 27, 2007 in Int'l Application No. PCT/IL2007/000343.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.
Int'l Search Report Issued Oct. 17, 2005 in Int'l Application No. PCT/IL2005/000376.
Int'l Preliminary Report on Patentability Issued Jun. 19, 2006 in Int'l Application No. PCT/IL2005/000376.
Written Opinion of ISR Issued Jun. 19, 2006 in Int'l Application No. PCT/IL2005/000376.
Int'l Search Report Issued Aug. 25, 2008 in Int'l Application No. PCT/IL2008/000517.
Written Opinion of the ISR Issued Oct. 17, 2009 in Int'l Application No. PCT/IL08/00517.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued Jan. 20, 2010 in JP Application No. 2007-510229.
Office Action Issued Apr. 20, 2010 in U.S. Appl. No. 11/997,569.

(56) References Cited

OTHER PUBLICATIONS

Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Office Action issued Jun. 1, 2010 in U.S. Appl. No. 11/568,421.
Office Action issued Nov. 12, 2010 in U.S. Appl. No. 29/334,697.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL: <http://www.ilpatsearch.justrice.gov.il/UI/RequestsList.aspx>. (1 page).
Int'l Search Report issued Nov. 25, 2010 in Int'l Application No. PCT/IL2010/000530.
Office Action issued Feb. 7, 2011 in U.S. Appl. No. 12/783,194.
Office Action issued Dec. 20, 2010 in U.S. Appl. No. 12/063,176.
Office Action issued Dec. 13, 2010 in U.S. Appl. No. 12/293,122.
Office Action issued Nov. 29, 2010 in U.S. Appl. No. 11/568,421.
Office Action issued Dec. 23, 2010 in U.S. Appl. No. 29/334,696.
Int'l Search Report issued on Mar. 17, 2011 in Int'l Application No. PCT/IL2010/000854.
Overview—Silicone Rubber [retrieved from http://www.knovel.com/web/portal/browse/display?_EXT_KNOVEL_DISPLAY_bookid=1023&VerticalID=0 on Feb. 9, 2011], [Retrieved on Sep. 2, 2011].
Int'l Search Report issued on Mar. 17, 2011 in Int'l Application No. PCT/IL2010/00915.
Office Action Issued May 12, 2011 in U.S. Appl. No. 12/063,176.
Office Action issued Jul. 11, 2011 in U.S. Appl. No. 12/293,122.
Intl Search Report issued Jul. 12, 2011 in Int'l Application No. PCT/IL2011/000187.
Int'l Search Report issued Jul. 12, 2011 in Int'l Application No. PCT/IL2011/000186.
Office Action issued Aug. 3, 2011 in JP Application No. 2008-525719.
Int'l Search Report issued Oct. 7, 2011 in Int'l Application No. PCT/IL2011/000511.
Int'l Search Report issued Mar. 6, 2012 in Int'l Application No. PCT/IL2011/000834; Written Opinion.
Office Action issued Mar. 1, 2012 in JP Application No. 2007-510229.
Int'l Search Report issued Mar. 7, 2012 in Int'l Application No. PCT/IL2011/000829; Written Opinion.
Office Action issued Mar. 13, 2012 in CA Application No. 2,563,643.
Office Action issued Mar. 1, 2012 in CN Application No. 2008801108283.4.

* cited by examiner

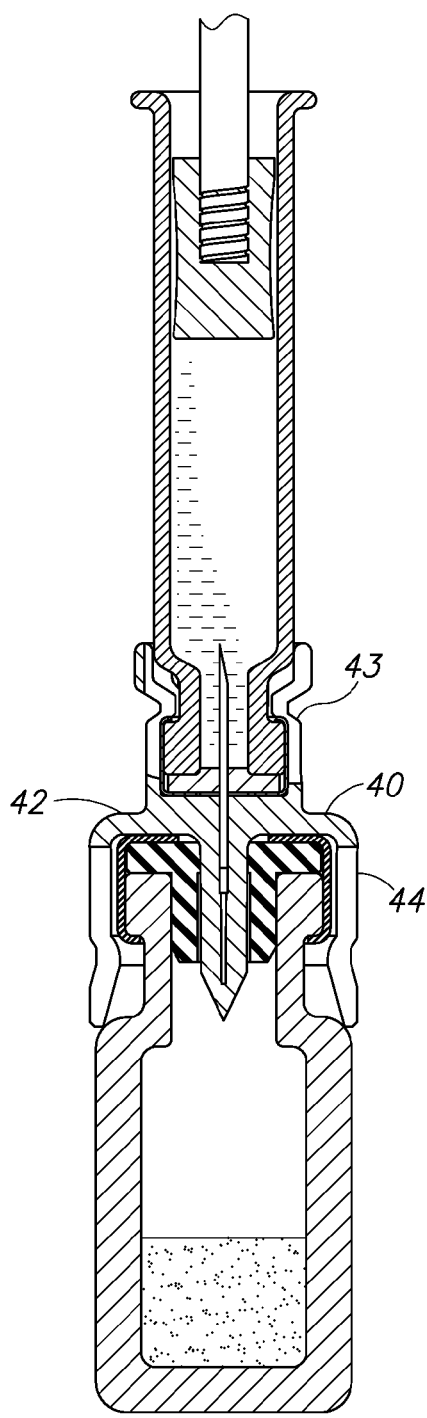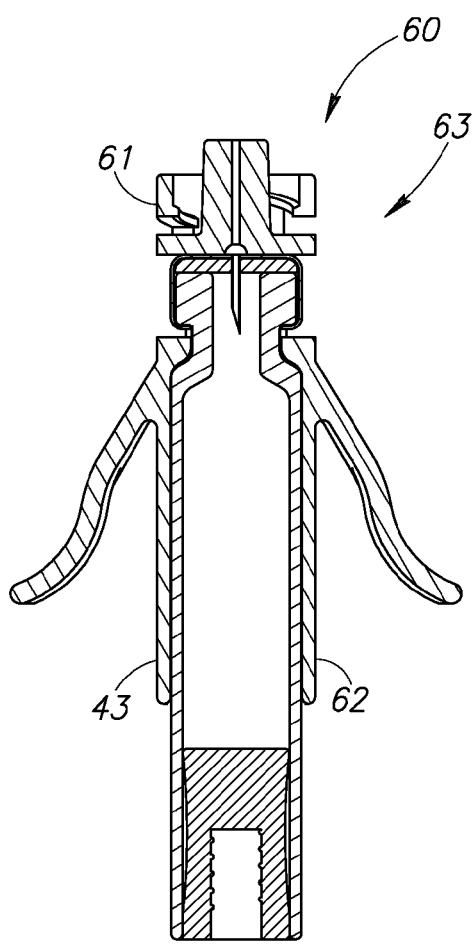
FIG.3
(PRIOR ART)
FIG.4
(PRIOR ART)

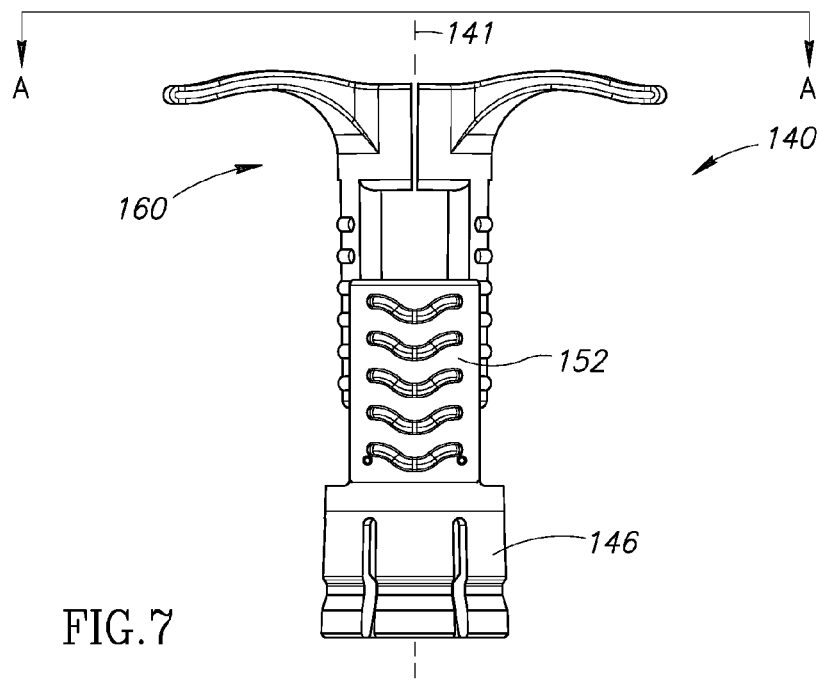
FIG.7
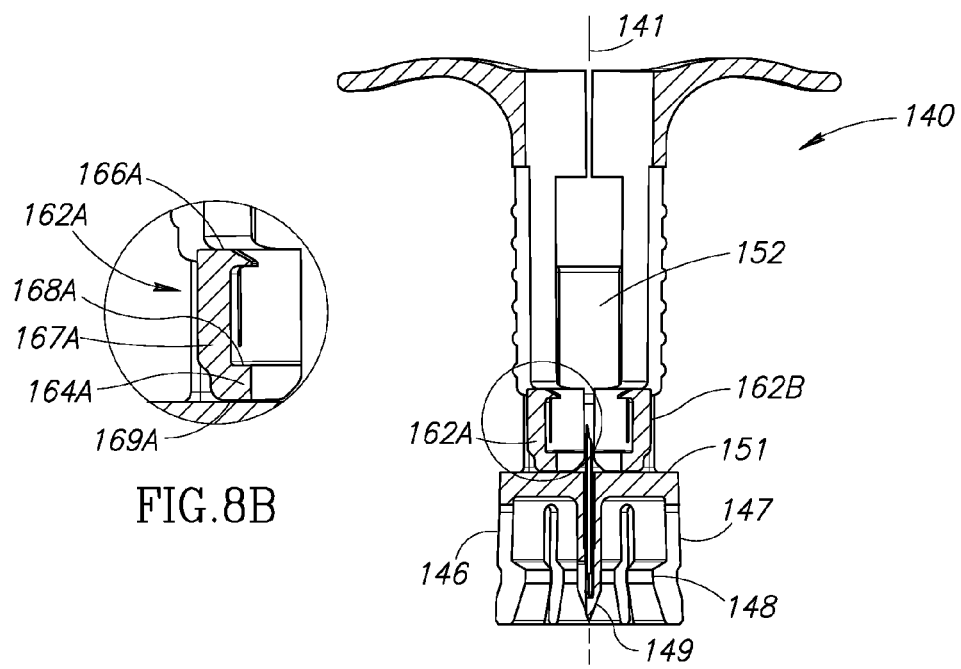
FIG.8B
FIG.8A

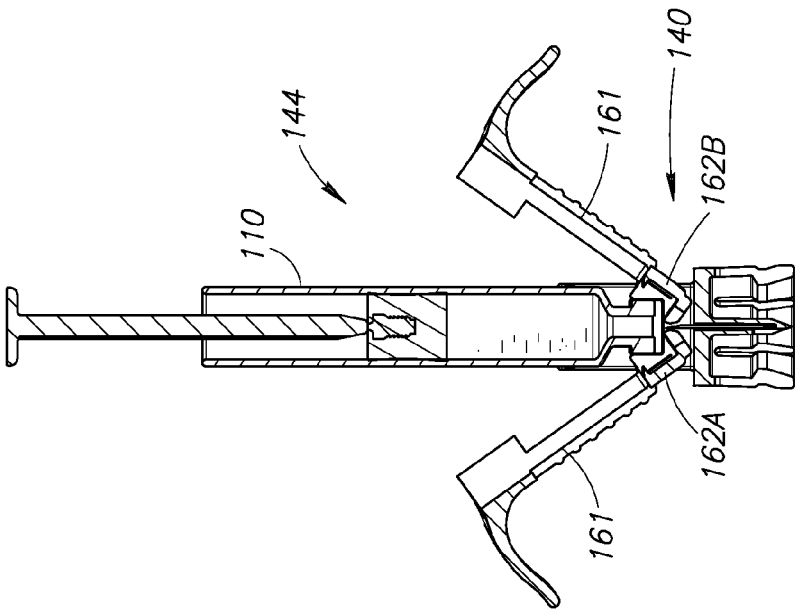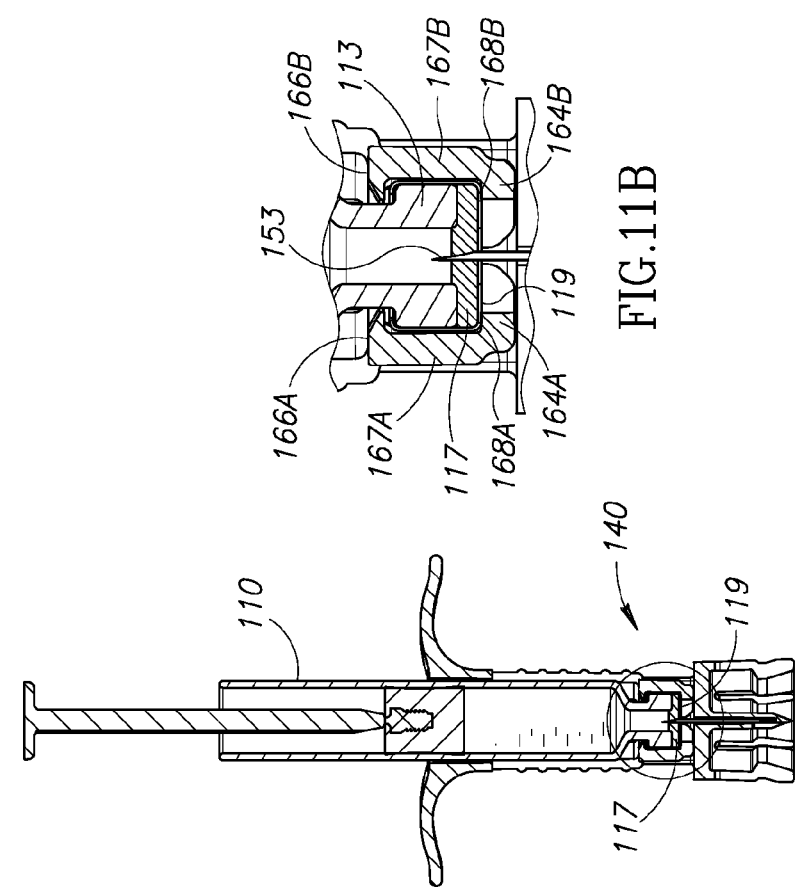

FLUID TRANSFER DEVICES HAVING CARTRIDGE PORT WITH CARTRIDGE EJECTION ARRANGEMENT

FIELD OF THE INVENTION

The invention relates to fluid transfer devices for filling a cartridge with a liquid drug dosage.

BACKGROUND OF THE INVENTION

Auto-injectors for self-administration of liquid drugs such as insulin typically employ so-called carpules or cartridges including an open ended tube hermetically sealed by a rubber septum at a leading cartridge end and a slidable seal at an opposite trailing cartridge end. Cartridges can contain a single liquid drug dosage or a multiple liquid drug dosage. Home users are typically supplied with cartridges pre-filled with a liquid drug dosage but may be supplied with empty cartridges requiring a manual cartridge filling procedure for filling with a liquid drug dosage. The manual cartridge filling procedure includes the following steps: A user prepares a syringe with a liquid drug dosage, mounts a needle on the syringe, punctures the cartridge's rubber septum and injects the liquid drug dosage into the cartridge. The user may have an additional step of reconstituting a liquid drug dosage from a powdered medicament.

Commonly owned PCT International Application No. PCT/IL2007/000343 entitled Fluid Transfer Devices for Use with Cartridges and published under PCT International Publication No. WO 2007/105221 discloses fluid transfer devices discussed hereinbelow for use with needleless syringes and cartridges for assisting a manual cartridge filling procedure.

Commonly owned PCT International Application No. PCT/IL2010/000530 entitled Fluid Transfer Devices for Filling a Cartridge with Liquid Drug Dosage and published under PCT International Publication No. WO 2011/004360 discloses fluid transfer devices discussed hereinbelow for use with cartridges and vials for assisting a manual cartridge filling procedure. WO 2011/004360 discloses provisioning otherwise conventional cartridges including a slidable seal with a releasable attachment arrangement and a manual push rod for releasable attachment to the slidable seal for enabling manual displacement of same for injection and aspiration purposes. Suitable releasable attachment arrangements include inter alia a screw thread arrangement, and the like.

There is a need for fluid transfer devices for facilitating a manual cartridge filling procedure for filling a cartridge with a liquid drug dosage and manual sliding ejection of the filled cartridge for subsequent deployment in an auto-injector.

SUMMARY OF THE INVENTION

The present invention is directed toward fluid transfer devices for use in manual cartridge filling procedures for filling cartridges with liquid drug dosages from medicament containing vials. The fluid transfer devices include a double ended main body having a longitudinal axis, a vial port for telescopic receiving a drug vial and a cartridge port for slidingly receiving a leading cartridge end. The cartridge ports include a cartridge securing arrangement for releasably securing a leading cartridge end in a cartridge port and a cartridge ejection arrangement for at least partially ejecting a filled cartridge therefrom for assisting its complete sliding ejection. The fluid transfer devices preferably include a pair of outward transverse directed finger supports for enabling a user to use them in a similar manner as a syringe.

Cartridge ports can include a combined cartridge securing and ejection arrangement including one or more lever members for securing a cartridge in a cartridge port and imparting a levering action for at least partially ejecting a filled cartridge therefrom. Alternatively, the cartridge ports can include a discrete cartridge securing arrangement and a discrete cartridge ejection arrangement. Such a discrete cartridge ejection arrangement can include one or more cartridge ejection members which are biased into a primed state on manual sliding insertion of a cartridge into a secured position in a cartridge port. On manual release of the cartridge securing arrangement, the one or more cartridge ejection members revert to their unbiased state for at least partially ejecting a filled cartridge from a cartridge port.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which:

FIG. 3 corresponds with hitherto mentioned PCT International Publication No. WO 2011/004360 FIG. 2;

FIG. 4 corresponds with hitherto mentioned PCT International Publication No. WO 2011/004360 FIG. 6;

FIG. 7 is a front elevation view of FIG. 5's fluid transfer device with its combined cartridge securing and ejection arrangement in an initial cartridge insertion position;

FIG. 8A is a longitudinal cross section of FIG. 5's fluid transfer device along line A-A in FIG. 7;

FIG. 8B is an enlarged view of the encircled area in FIG. 8A showing a leading lever member end of the combined cartridge securing and ejection arrangement;

FIG. 11A is longitudinal cross section of FIG. 5's fluid transfer device showing a cartridge secured in its combined securing and ejection arrangement;

FIG. 11B is an enlarged view of the encircled area in FIG. 11A showing the securing of the leading cartridge end;

FIG. 12 is a longitudinal cross section of FIG. 5's fluid transfer device showing partial ejection of the cartridge from the cartridge port;

DETAILED DESCRIPTION OF PREFERRED EMBODIMENTS OF THE INVENTION

Figure 1:
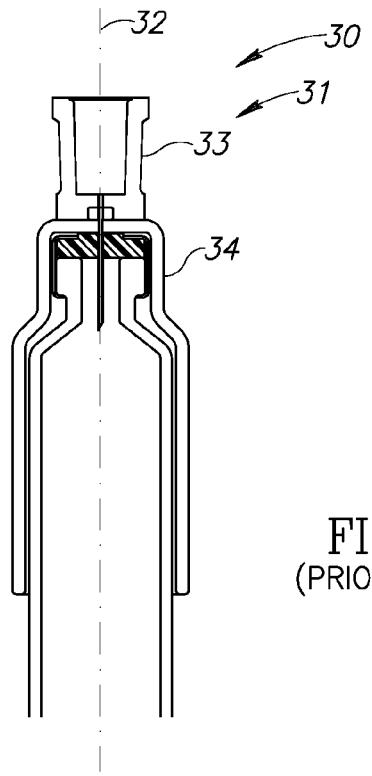
FIG. 1 corresponds with hitherto mentioned PCT International Publication No. WO 2007/105221 FIG. 2.
Figure 2:
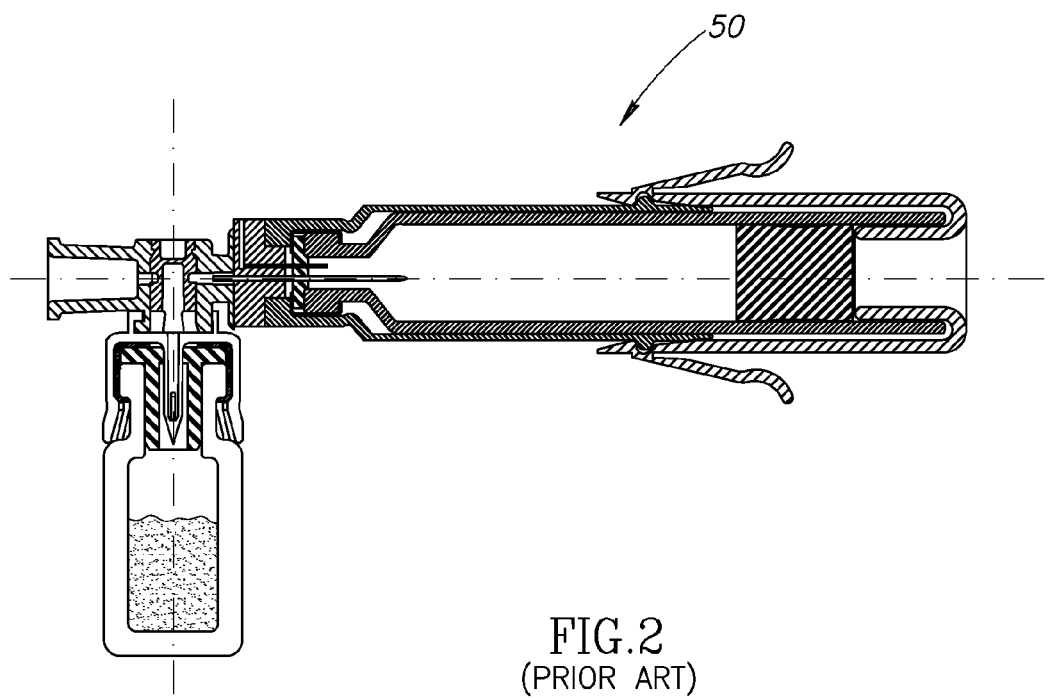
FIG. 2 corresponds with hitherto mentioned PCT International Publication No. WO 2007/105221 FIG. 5.

FIG. 1 corresponds with hitherto mentioned WO 2007/105221 FIG. 2 showing a fluid transfer device 30 including a double ended main body 31, a longitudinal axis 32, a syringe port 33 for receiving a needleless syringe and a cartridge port 34 for telescopically receiving a cartridge.

Figure 5:
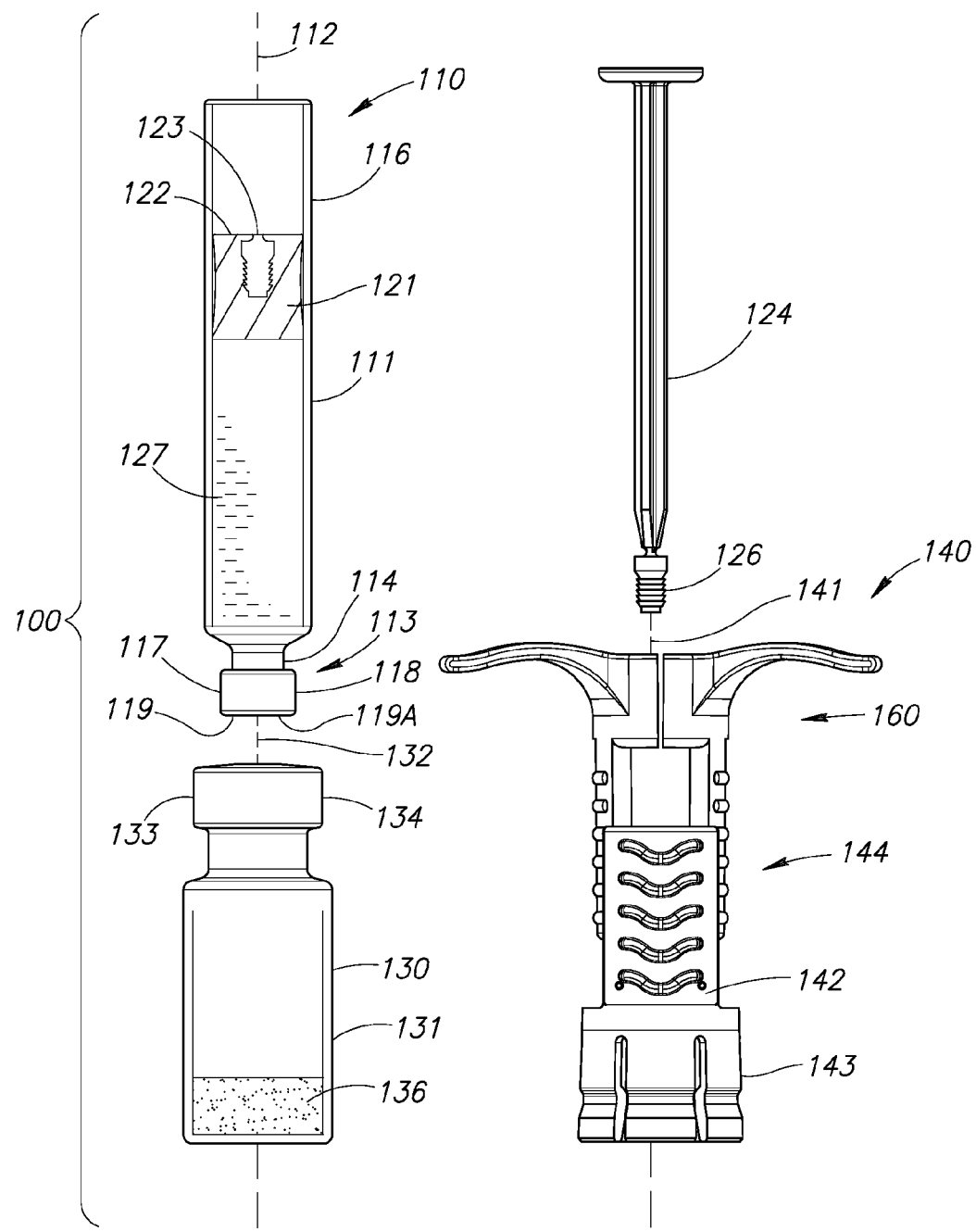
FIG. 5 is a pictorial representation of a kit including a pre-filled cartridge, a push rod, a drug vial and a fluid transfer device having a combined cartridge securing and ejection arrangement in accordance with a first preferred embodiment of the present invention.

FIG. 2 corresponds with WO 2007/105221 FIG. 5 showing a fluid transfer device 50 similar in construction and operation to the fluid control device 30 with rotationally detachable vial adapters as disclosed in commonly owned U.S. Pat. No. 6,238,372 to Zinger et al.'s FIGS. 11 to 15.

FIG. 3 corresponds with WO 2011/004360 FIG. 2 showing a fluid transfer device 40 including a double ended main body 42 having a cartridge port 43 for sliding receiving a cartridge's leading end and a vial port 44 for snap fitting onto a vial.

Figure 6:
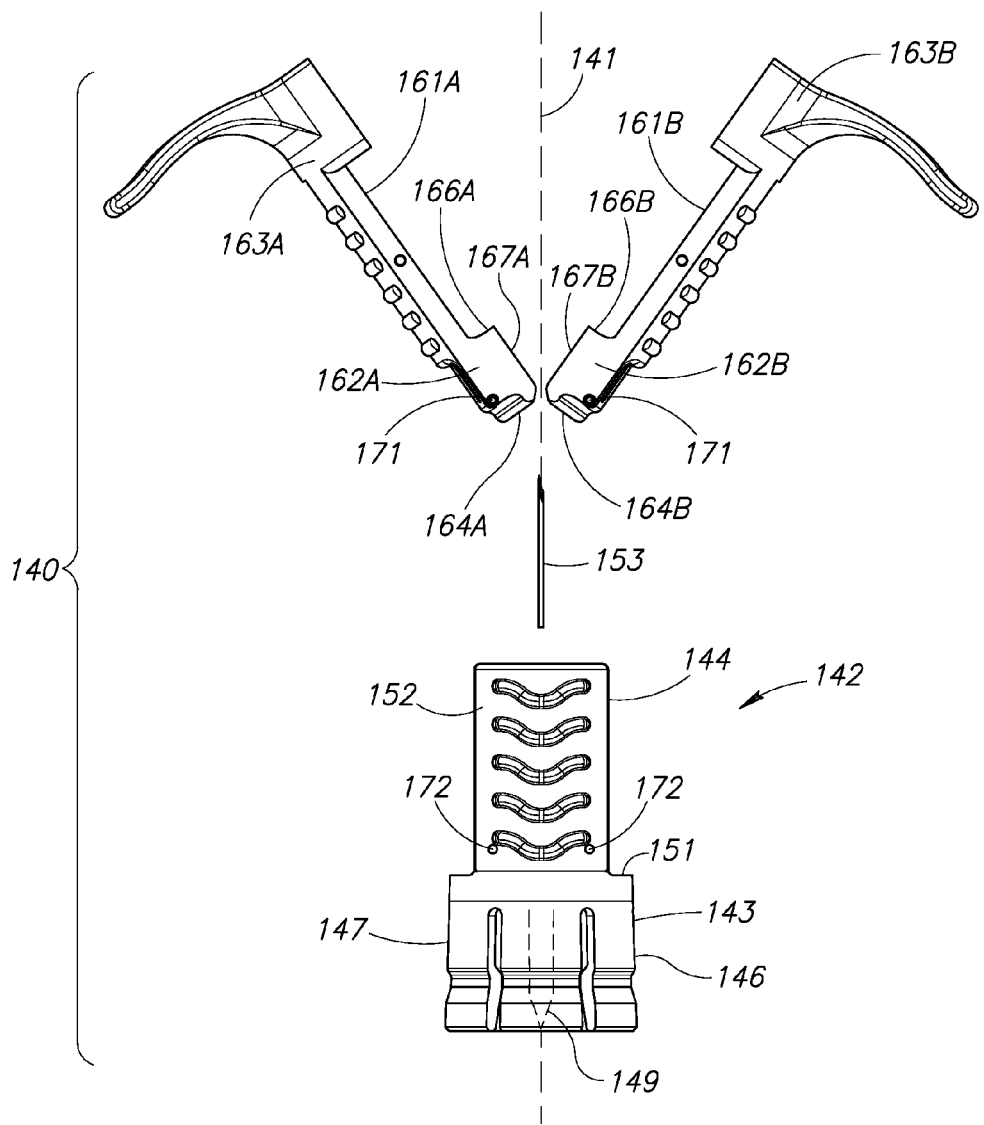
FIG. 6 is an exploded view of FIG. 5's fluid transfer device.
Figure 9:
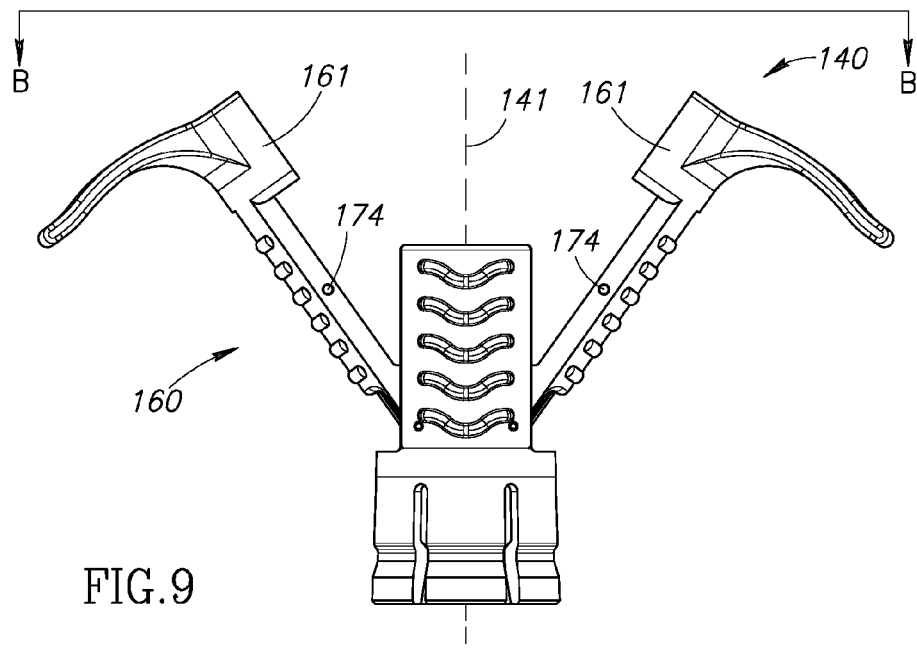
FIG. 9 is a front elevation view of FIG. 5's fluid transfer device with its combined cartridge securing and ejection arrangement in a final cartridge ejection position.
Figure 10:
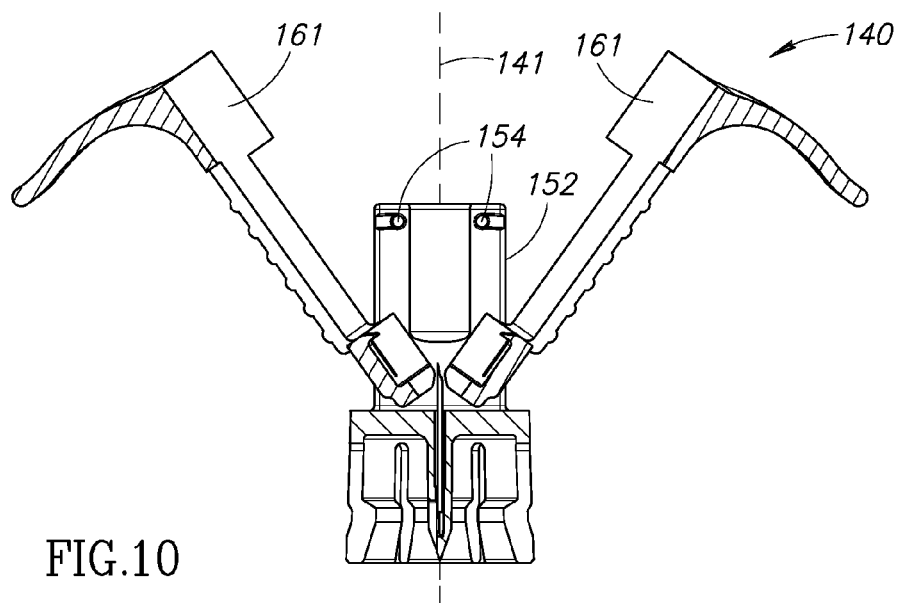
FIG. 10 is a longitudinal cross section of FIG. 5's fluid transfer device along line B-B in FIG. 9.

FIG. 4 corresponds with WO 2011/004360 FIG. 6 showing a fluid transfer device 60 including a male connector 61, an open ended cartridge holder 62 for slidingly receiving a cartridge and a finger operated cartridge snap fit arrangement 63 for initially snap fitting onto a cartridge on its sliding insertion into the cartridge holder 62 and enabling a user to manually release the cartridge for enabling the cartridge to be freely slidingly withdrawn from the cartridge holder 62.

FIG. 5 shows a kit 100 including a pre-filled cartridge 110, a push rod 124 having a screw threaded leading end 126, a drug vial 130 and a fluid transfer device 140 for use in a manual cartridge filling procedure for filling the cartridge 110 with a liquid drug dosage.

FIGS. 6 to 12 show the cartridge 110 includes an open ended tube 111 having a longitudinal axis 112, a small diameter leading cartridge end 113, an intermediate neck 114 and a wide diameter trailing cartridge end 116. The leading cartridge end 113 is hermetically sealed by a rubber cartridge septum 117 capped by a metal band 118. The leading cartridge end 113 has a forwardmost cartridge surface 119 including an exposed 2 mm to 3 mm diameter circular rubber surface 119A. The trailing end 116 is hermetically sealed by a slidable seal 121. The slidable seal 121 has an exposed trailing surface 122 formed with a screw thread blind bore 123 for screw thread attachment with the push rod's screw threaded leading end 126. The cartridge 110 is pre-filled with liquid contents 127. The liquid contents 127 are typically diluent for reconstituting a powder drug. Alternatively, the liquid contents 127 can include an active component.

The drug vial 130 includes an open topped vial bottle 131 having a longitudinal axis 132 and hermetically sealed by a vial stopper 133 capped by a metal band 134. The drug vial 130 can contain a powder or liquid drug contents 136. Powdered drug contents 136 are typically stored under negative pressure and require reconstitution prior to administration. Alternatively, the drug vial 130 can contain a liquid drug suitable for direct transfer to an empty cartridge.

The fluid transfer device 140 has a longitudinal axis 141 and includes a double ended main body 142 having a vial port 143 for telescopically receiving a drug vial 130 and a cartridge port 144 for slidingly receiving a leading cartridge end 113.

The vial port 143 includes a slotted skirt 146 with a plurality of flex members 147 having inwardly directed ridges 148 for snap fitting onto the drug vial 130 and a puncturing cannula 149 co-axial with the fluid transfer device's longitudinal axis 141 for puncturing the vial stopper 133 on snap fit insertion of the drug vial 130 thereinto.

The cartridge port 144 includes a base surface 151 formed with a pair of opposite cartridge supports 152 for providing axial support to the leading cartridge end 113 on being slidingly inserted thereinto. The cartridge port 144 also includes a puncturing member 153 for puncturing the cartridge septum 117 on sliding insertion of a leading cartridge end 113 thereinto. The puncturing member 153 is preferably constituted by a metal needle having an outer diameter of, say, about 0.5 mm. The puncturing member 153 is also co-axial with the fluid transfer device's longitudinal axis 141 and in flow communication with the puncturing cannula 149 to enable direct fluid communication between a cartridge 110 and a drug vial 130 in an assemblage of the fluid transfer device 140, the cartridge 110 and the drug vial 130. The cartridge support pair 152 has indents 154 (see FIG. 10).

The cartridge port 144 is additionally provisioned with a combined cartridge securing and ejection arrangement 160 for releasably securing a leading cartridge end 113 therein and at least partially ejecting a cartridge 110 filled with a liquid drug dosage therefrom. The combined cartridge securing and ejection arrangement 160 includes a pair of opposite elongated lever members 161A and 161B. The lever member pair 161 extend beyond the cartridge supports 152 and are co-directional with the longitudinal axis 141 in an initial cartridge insertion position to assist guiding manual sliding insertion of the cartridge 110 into the cartridge port 144 (see FIGS. 5, 7 and 8A).

The lever member pair 161A and 161B correspondingly have leading lever member ends 162A and 162B adjacent the vial port 143 and trailing lever member ends 163A and 163B remote from the vial port 143. The lever member pair 161 is pivotal on the main body 142 at their leading lever member ends 162 for being manually levered from their initial cartridge insertion position to being outwardly inclined with respect to the longitudinal axis 141 in a final cartridge ejection position (see FIGS. 9, 10 and 12).

The leading lever member end pair 162A and 162B have correspondingly forwardmost rims 164A and 164B, rearmost rims 166A and 166B and intermediate sections 167A and 167B. The forwardmost rims 164 have uppermost surfaces 168 and lowermost surfaces 169 respectively facing away and towards the vial port 143. The forwardmost rims 164 are formed with indents 171 for snap fit receiving pins 172 formed on the opposite cartridge supports 152 for enabling the pivotal action of the lever member pair 161. In the initial cartridge insertion position, the forwardmost rims 164 overlie the base surface 151 and define a separation therebetween which is less than the leading cartridge end 113's diameter.

The lever member pair 161 are dimensioned such that they extend midway along the cartridge 110 on its full insertion into the cartridge port 144 and its trailing lever member ends 163A and 163B are formed with outward transverse directed finger supports 173A and 173B with respect to the longitudinal axis 141 for enabling use of the fluid transfer device 140 in a similar manner as a syringe.

The lever member pair 161 is formed with projections 174 for engaging the indents 154 on the cartridge support pair 152 for securing the lever member pair 161 in their initial co-directional position during the sliding insertion of the cartridge 110 into the cartridge port 144.

FIGS. 11A and 11B show a forwardmost cartridge surface 119 abuts against the uppermost surfaces 168 of the forwardmost rims 164 on full insertion of its leading cartridge end 113 into the cartridge port 144 to be spaced apart from the base surface 151. FIGS. 11A and 11B also show the intermediate sections 167 are dimensioned such that the rearmost rims 166 snap fit onto the leading cartridge end 113 for securing purposes.

FIG. 12 shows manual levering of the lever member pair 161 causes them to pivot at their leading lever member ends 162 such that their forwardmost rims 164 act against the cartridge's forwardmost cartridge surface 119 to at least partially eject the cartridge 110 from the cartridge port 144 for assisting its complete manual sliding ejection therefrom.

Figure 13D:
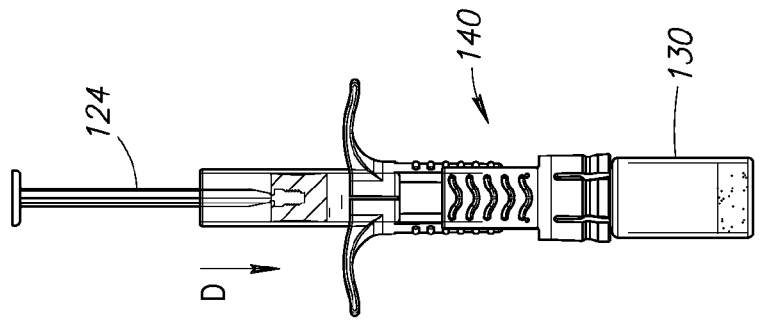
FIGS. 13A to 13H show the use of FIG. 5's fluid transfer device for filling a cartridge with a reconstituted liquid drug dosage.
Figure 13C:
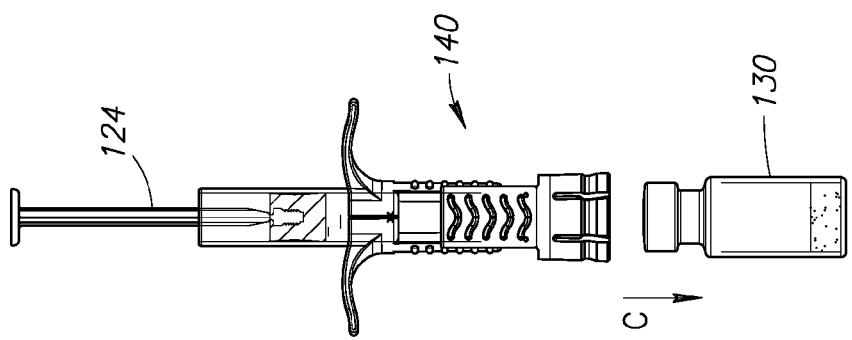
Figure 13B:
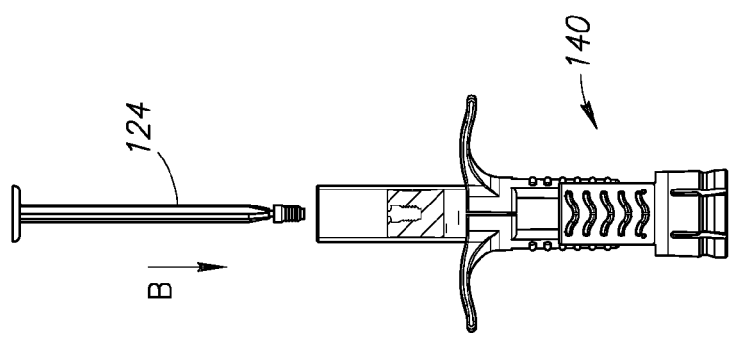
Figure 13A:
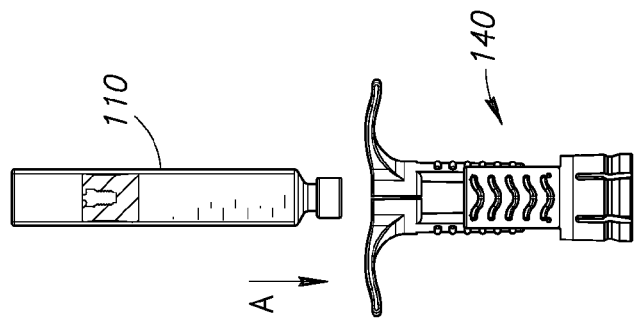

FIGS. 13A to 13H show the use of the kit 100 to reconstitute a liquid drug dosage and aspirate same into the cartridge as follows:

FIG. 13A shows a user inserting a cartridge pre-filled with diluent into the cartridge port as depicted by arrow A.

FIG. 13B shows a user screw threading a push rod into the pre-filled cartridge as depicted by arrow B.

FIG. 13C shows a user snap fitting the vial port onto a drug vial as depicted by arrow C.

FIG. 13D shows a user injecting the cartridge's contents into the vial for reconstitution purposes as depicted by arrow D for reconstituting the powder drug in the drug vial to form a reconstituted liquid drug LD.

Figure 13H:
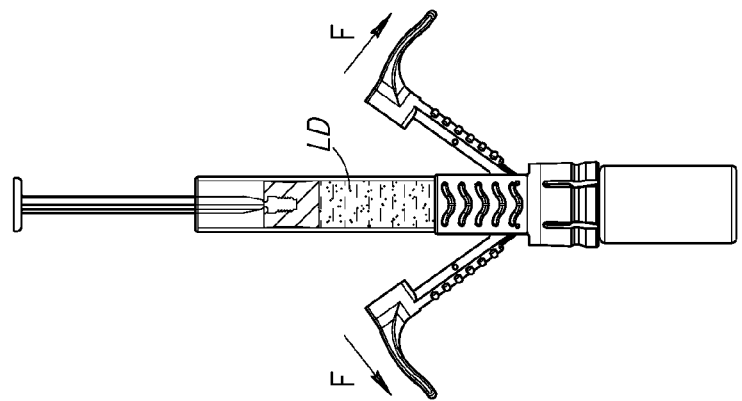
Figure 13G:
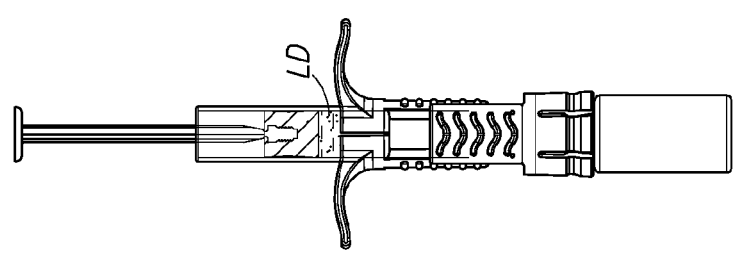
Figure 13F:
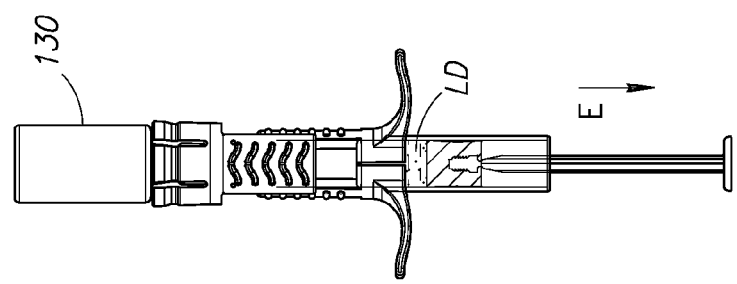
Figure 13E:
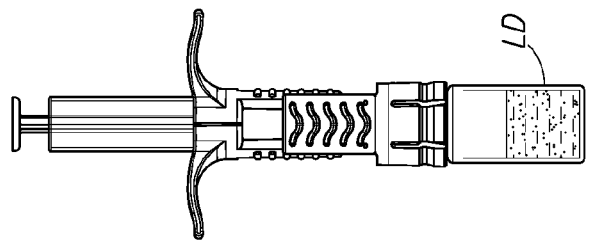

FIG. 13E shows the drug vial filled with the liquid drug LD.

FIG. 13F shows a user inverting the assemblage of the fluid transfer device, the drug vial and the cartridge and a user aspirating the liquid drug LD into the cartridge as depicted by arrow E.

FIG. 13G shows a user inverting the assemblage.

FIG. 13H shows a user manually levering the lever member pair outwards relative to the longitudinal axis as depicted by arrows F to partially eject the filled cartridge from the cartridge port. The filled cartridge can be readily completely slidingly ejected from the cartridge port.

Figure 14:
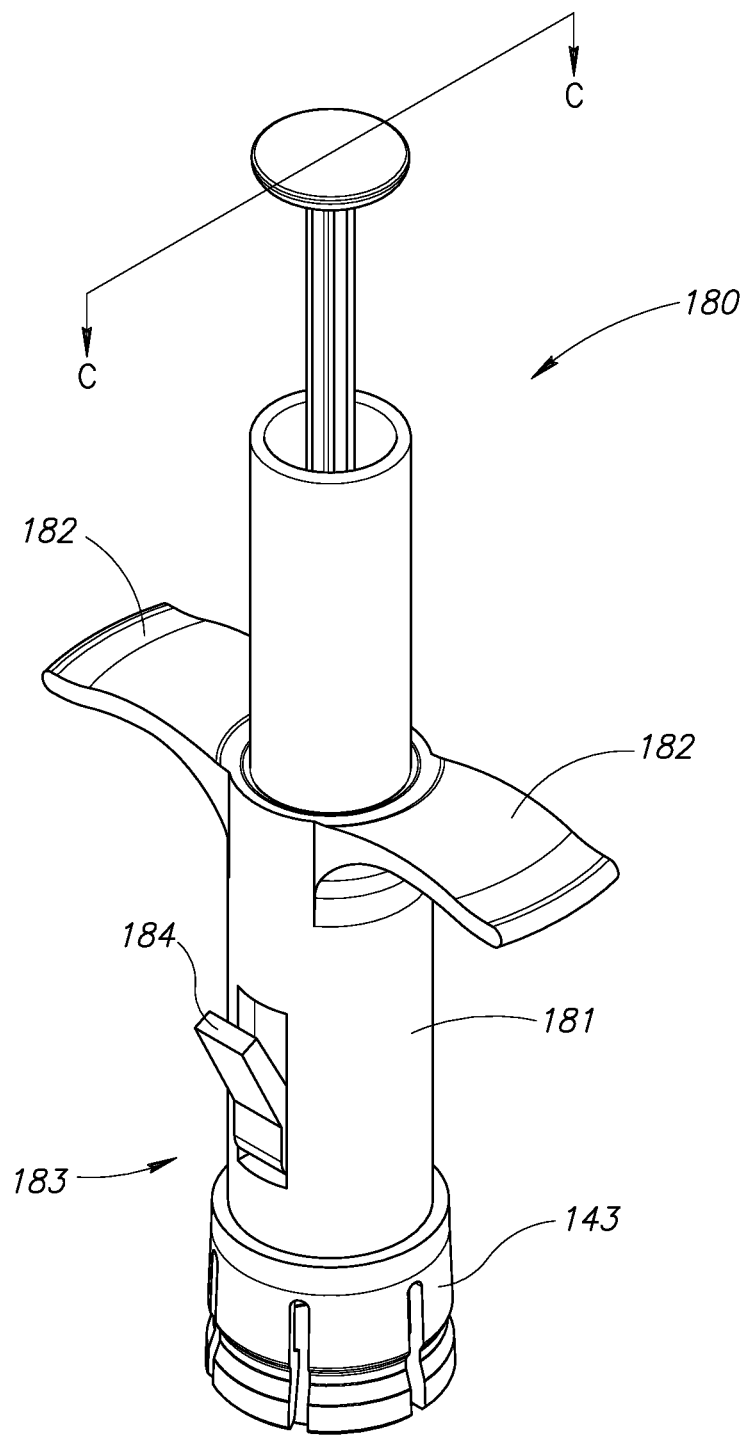
FIG. 14 is a front perspective view of a fluid transfer device including a combined cartridge securing and ejection arrangement in accordance with a second preferred embodiment of the present invention.
Figure 15A:
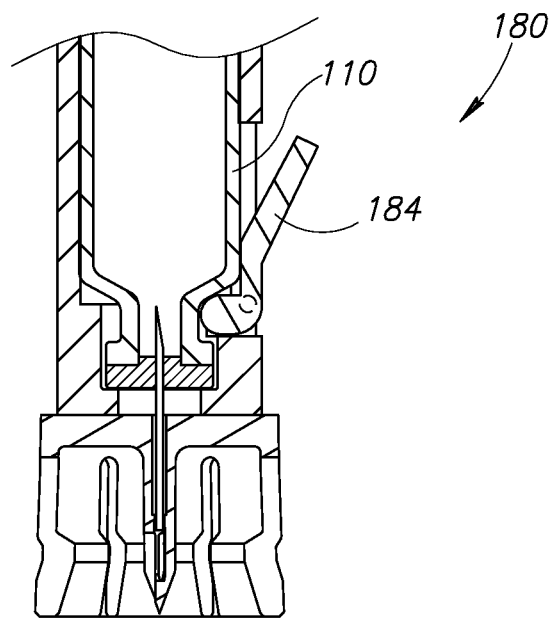
FIG. 15A is a longitudinal cross section of FIG. 14's fluid transfer device along line C-C in FIG. 14 on sliding insertion of a cartridge into its cartridge port.
Figure 15B:
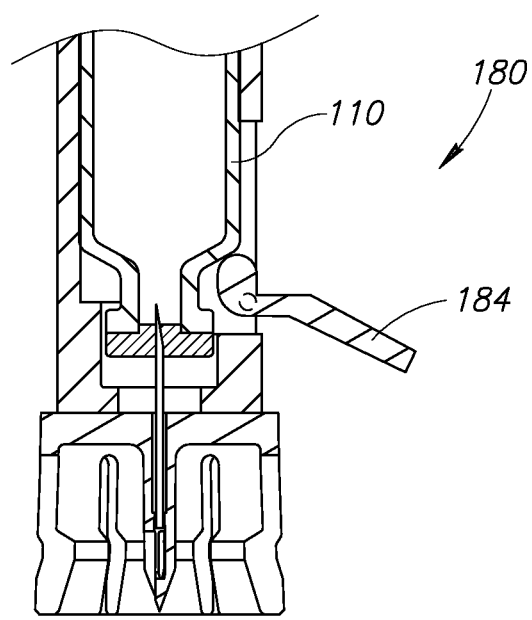
FIG. 15B is a longitudinal cross section of FIG. 14's fluid transfer device along line C-C in FIG. 14 on manual operation of its combined cartridge securing and ejection arrangement for at least partially ejecting the cartridge from the cartridge port.

FIGS. 14 and 15 show a fluid transfer device 180 similar in construction and operation to the fluid transfer device 140. The former 180 differs from the latter 140 insofar as the former 180 includes an elongated cartridge port 181 extending about midway along a cartridge 110 on its full insertion thereinto and integrally formed with a pair of outward transverse directed finger supports 182 for enabling use of the fluid transfer device 180 in a similar manner as a syringe. The fluid transfer device 180 includes a combined cartridge securing and ejection arrangement 183 with a single lever member 184 for securing and ejection purposes. The lever member 184 at least partially ejects a filled cartridge 110 by urging against a leading end of its open ended tube 111 as opposed to the forwardmost cartridge surface 119 in the case of former 140.

Figure 16:
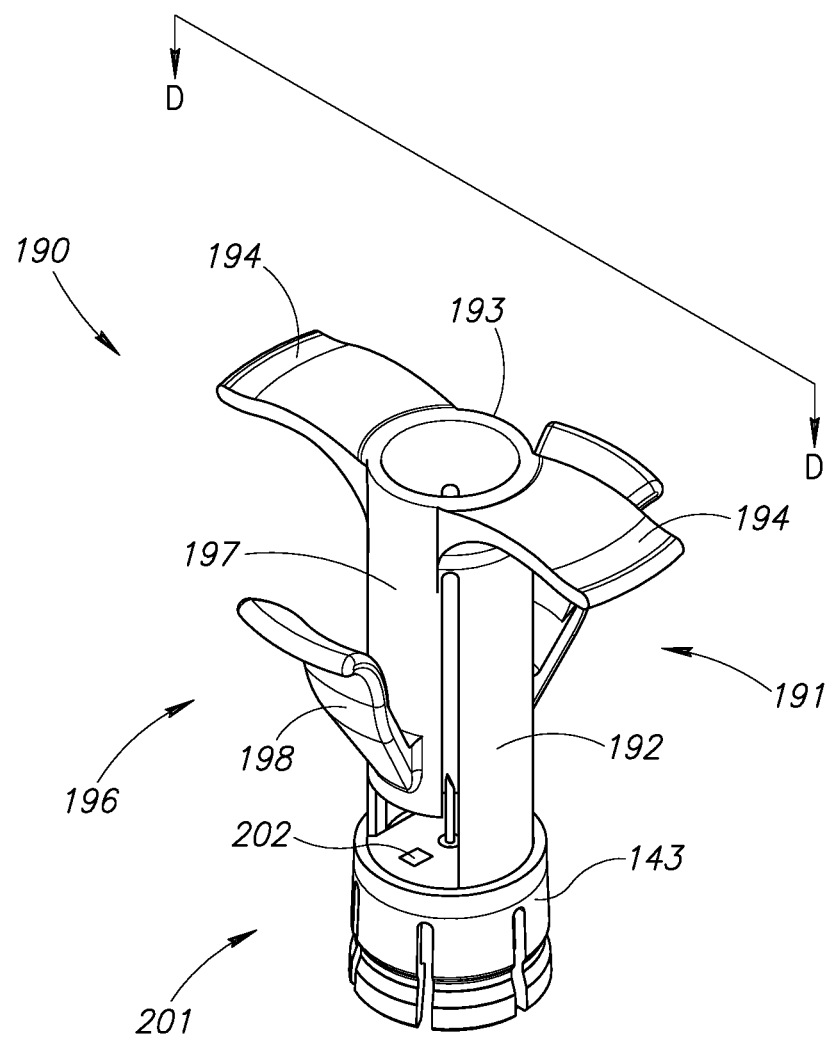
FIG. 16 is a front perspective view of a fluid transfer device including a discrete cartridge securing arrangement and a discrete cartridge ejection arrangement in accordance with a third preferred embodiment of the present invention.
Figures 17, 18:
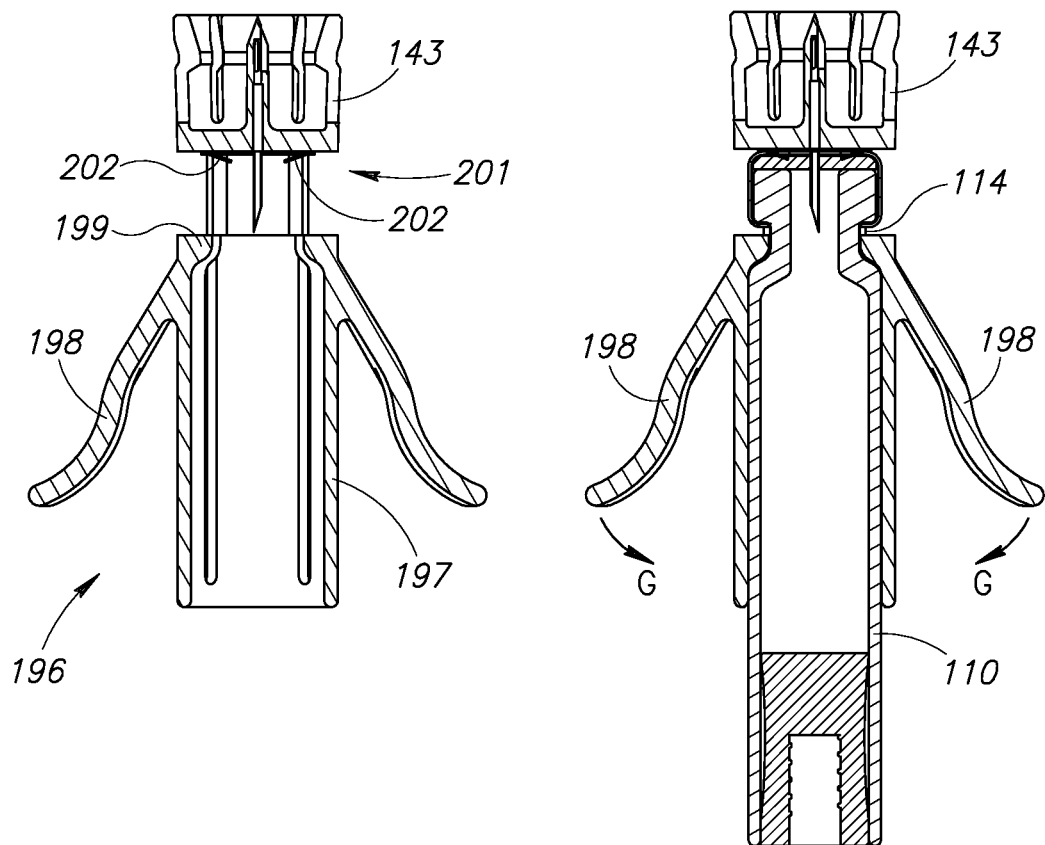
FIG. 17 is a longitudinal cross section of FIG. 16's fluid transfer device along line D-D in FIG. 16.
FIG. 18 is a longitudinal cross section of FIG. 16's fluid transfer device along line D-D in FIG. 16 on sliding insertion of a cartridge into its cartridge port to prime its cartridge ejection arrangement.

FIGS. 16 to 18 show a fluid transfer device 190 similar in construction and operation to the fluid transfer device 140. The former 190 differs from the latter 140 insofar as the former 190 includes an elongated cartridge port 191 with opposite cartridge supports 192 terminating at an annular cartridge port base 193 formed with a pair of outward transverse directed finger supports 194 for enabling use of the fluid transfer device 190 in a similar manner as a syringe. The elongated cartridge port 191 is formed with a discrete cartridge securing arrangement 196 for securing a cartridge 110 in the cartridge port 191. The cartridge securing arrangement 196 is similar to WO 2011/004360 FIG. 6's finger operated cartridge snap fit arrangement 63 (see FIG. 4) and includes a pair of opposite flex members 197 resiliently flexibly mounted at the cartridge port base 193. The flex members 197 each have an outwardly directed finger operated member 198 and terminate in an inwardly directed ridge 199 for snap fit insertion against a cartridge's intermediate neck 114 on sliding insertion of a cartridge 110 into the cartridge port 191. Depression of the pair of finger operated members 198 towards one another as denoted by arrows G outwardly urges the inwardly directed ridges 199 thereby releasing a cartridge 110.

The fluid transfer device 190 also includes a discrete cartridge ejection arrangement 201 for selectively at least partially ejecting a cartridge 110 from the cartridge port 191 for assisting complete manual sliding ejection of a filled cartridge therefrom. The discrete cartridge ejection arrangement 201 includes at least one cartridge ejection member 202 biased into a primed state on manual sliding insertion of a leading cartridge end 113 into the cartridge port 191 into a secured position secured by the discrete cartridge securing arrangement 196. The cartridge ejection members 202 can be constituted by spring leaf members, springs, and the like. The cartridge ejection arrangement 201 includes a pair of spring leaf members 202. On manual releasing the cartridge securing arrangement 196 by depressing the pair of finger operated members 198, the cartridge ejection members 202 outwardly urge the leading cartridge end 113 from the cartridge port 191 for assisting complete manual sliding ejection of the filled cartridge.

While the invention has been described with respect to a limited number of embodiments, it will be appreciated that many variations, modifications, and other applications of the invention can be made within the scope of the appended claims.

The invention claimed is:

1. A fluid transfer device for use with a cartridge and a drug vial for filling the cartridge with a liquid drug dosage, the cartridge including an open ended tube having a leading cartridge end and a trailing cartridge end, the leading cartridge end sealed by a cartridge septum and the trailing cartridge end sealed by a slidable seal, the leading cartridge end having a forwardmost cartridge surface, the drug vial including a drug vial bottle containing a drug component and having a drug vial opening sealed by a drug vial stopper, the fluid transfer device comprising:

a double ended main body having a longitudinal axis and including:

a vial port for telescopically receiving the drug vial, the vial port having a puncturing cannula for puncturing the drug vial stopper for flow communication with the drug vial bottle; and a cartridge port having:

i) a puncturing needle for puncturing the cartridge septum for flow communication with the open ended tube on manual sliding insertion of the cartridge thereinto towards said vial port, said puncturing cannula being in flow communication with said puncturing needle for enabling a manual cartridge filling procedure for filling the cartridge with the liquid drug dosage, ii) a cartridge securing arrangement for releasably securing the cartridge in said cartridge port on said manual sliding insertion thereinto, and iii) a cartridge ejection arrangement for at least partially ejecting a filled cartridge from said cartridge port for assisting complete sliding ejection of the filled cartridge therefrom.

2. The device according to claim 1 wherein said cartridge securing arrangement and said cartridge ejection arrangement are formed as a combined cartridge securing and ejection arrangement said combined cartridge securing and ejection arrangement having at least one lever member, each of said at least one lever member having a leading lever member end and a trailing lever member end correspondingly adjacent to and remote from said vial port, each of said at least one lever member being pivotal on said double ended main body at said leading lever member end for being manually levered from an initial cartridge insertion position co-directional with the longitudinal axis for enabling said manual sliding insertion into said cartridge port to a cartridge ejection position for said at least partially ejecting the filled cartridge from said cartridge port.

3. The device according to claim 2 wherein said combined cartridge securing and ejection arrangement includes a pair of opposite elongated lever members co-directional with the longitudinal axis and dimensioned for guiding said manual sliding insertion of the cartridge into said cartridge port.

4. The device according to claim 3 wherein said pair of opposite elongated lever members extend midway along the cartridge in said initial cartridge insertion position and said trailing lever member end of each lever member of said pair of opposite lever members includes an outward transverse directed finger support for enabling use of the fluid transfer device in a similar manner as a syringe.

5. The device according to claim 2 wherein said cartridge port is elongated and dimensioned to extend midway along the cartridge on said manual sliding insertion therein and formed with a pair of opposite outward transverse directed finger supports for enabling use of the fluid transfer device in a similar manner as a syringe.

6. The device according to claim 1 wherein said cartridge ejection arrangement includes at least one cartridge ejection member biased into a primed state on said securing the cartridge in said cartridge port whereupon, on manual releasing said cartridge securing arrangement, said at least one cartridge ejection member at least partially ejects the cartridge from said cartridge port.

7. The device according to claim 6 wherein said cartridge port is elongated and dimensioned to extend midway along the cartridge on said manual sliding insertion therein and formed with a pair of opposite outward transverse directed finger supports for enabling use of the fluid transfer device in a similar manner as a syringe.

* * * * *